US009528893B2

(12) United States Patent
Wang et al.

(10) Patent No.: US 9,528,893 B2
(45) Date of Patent: Dec. 27, 2016

(54) OPTICAL FIBER PRESSURE SENSOR WITH UNIFORM DIAPHRAGM AND METHOD OF FABRICATING SAME

(75) Inventors: Wenhui Wang, Lowell, MA (US); Xingwei Vivian Wang, Worcester, MA (US); Kai Sun, Acton, MA (US); Nan Wu, Lowell, MA (US)

(73) Assignee: University of Massachusetts, Boston, MA (US)

( * ) Notice: Subject to any disclaimer, the term of this patent is extended or adjusted under 35 U.S.C. 154(b) by 1268 days.

(21) Appl. No.: 13/381,256

(22) PCT Filed: Jun. 29, 2010

(86) PCT No.: PCT/US2010/040460
§ 371 (c)(1),
(2), (4) Date: Dec. 28, 2011

(87) PCT Pub. No.: WO2011/008559
PCT Pub. Date: Jan. 20, 2011

(65) Prior Publication Data
US 2012/0116255 A1    May 10, 2012

Related U.S. Application Data

(60) Provisional application No. 61/221,429, filed on Jun. 29, 2009.

(51) Int. Cl.
*G01L 9/00*    (2006.01)
*G01L 7/08*    (2006.01)

(52) U.S. Cl.
CPC .............. *G01L 7/086* (2013.01); *Y10T 156/10* (2015.01); *Y10T 156/1052* (2015.01)

(58) Field of Classification Search
None
See application file for complete search history.

(56) References Cited

U.S. PATENT DOCUMENTS 3,532,181 A   10/1970  DeMaria et al.
4,329,058 A    5/1982  James et al.
(Continued)

FOREIGN PATENT DOCUMENTS

EP    0 389071 B    1/1990
EP    1 078 227 B1  7/2002
(Continued)

OTHER PUBLICATIONS

Chandrasekaran, S. and Sundararajan, S., "Effect of microfabrication processes on surface roughness parameters of silicon surfaces", *Proceedings of the 31st International Conference on Metallurgical Coatings and Thin Films*, 188-189: 581-587 (Nov.-Dec. 2004).
(Continued)

*Primary Examiner* — Andre Allen
(74) *Attorney, Agent, or Firm* — Hamilton, Brook, Smith & Reynolds, P.C.

(57) ABSTRACT

An optical fiber sensor (100) can be used to measure pressure with high sensitivity and fine resolution. As a (108) at the end of the sensor expands or contracts, the spectrum of a beam reflected from the end of fiber shifts, producing a change linked to pressure exerted on the sensor. Novel aspects of the present inventive sensor include the direct bonding of a silica thin film diaphragm (110) to the optical fiber with localized or confined heating and a uniform thickness of the diaphragm. The resulting sensor has a diameter that matches the diameter of the optical fiber. Because the sensor is all silica, it does not from temperature-induced error. In addition, the sensor can be very sensitive because the diaphragm can be very thin; it can also make highly repeatable measurements due to its very uniform thickness.

20 Claims, 16 Drawing Sheets

(56) References Cited

U.S. PATENT DOCUMENTS

| | | | |
|---|---|---|---|
| 4,503,564 A | 3/1985 | Edelman | |
| 4,639,091 A | 1/1987 | Huignard et al. | |
| 4,652,744 A | 3/1987 | Bowers et al. | |
| 4,678,904 A | 7/1987 | Saaski et al. | |
| 4,682,500 A | 7/1987 | Uda | |
| 4,942,767 A | 7/1990 | Haritonidis et al. | |
| 5,087,124 A | 2/1992 | Smith et al. | |
| 5,101,664 A | 4/1992 | Hockaday et al. | |
| 5,247,490 A | 9/1993 | Goepel et al. | |
| 5,301,001 A | 4/1994 | Murphy et al. | |
| 5,324,282 A | 6/1994 | Dodick | |
| 5,365,789 A | 11/1994 | Totterdell et al. | |
| 5,381,231 A | 1/1995 | Tu | |
| 5,392,117 A | 2/1995 | Belleville et al. | |
| 5,528,367 A | 6/1996 | Putnam et al. | |
| 5,559,358 A | 9/1996 | Burns et al. | |
| 5,615,675 A | 4/1997 | O'Donnell et al. | |
| 5,747,705 A | 5/1998 | Herb et al. | |
| 5,891,747 A | 4/1999 | Farah | |
| 5,920,521 A | 7/1999 | Kromer et al. | |
| 5,944,687 A | 8/1999 | Benett et al. | |
| 6,066,098 A | 5/2000 | Masotti et al. | |
| 6,281,976 B1 | 8/2001 | Taylor et al. | |
| 6,304,686 B1* | 10/2001 | Yamate | G01L 9/0076 385/13 |
| 6,309,352 B1 | 10/2001 | Oraevsky et al. | |
| 6,322,557 B1 | 11/2001 | Nikolaevich et al. | |
| 6,328,482 B1 | 12/2001 | Jian | |
| 6,405,069 B1 | 6/2002 | Oraevsky et al. | |
| 6,513,390 B1 | 2/2003 | De La Puente et al. | |
| 6,519,376 B2 | 2/2003 | Biagi et al. | |
| 6,527,455 B2 | 3/2003 | Jian | |
| 6,567,173 B1 | 5/2003 | Johannesen | |
| 6,738,145 B2 | 5/2004 | Sherrer et al. | |
| 6,820,487 B2 | 11/2004 | Esashi et al. | |
| 6,925,213 B2 | 8/2005 | Boyd et al. | |
| 6,933,490 B1 | 8/2005 | Vidovic et al. | |
| 6,934,015 B1 | 8/2005 | Vidovic et al. | |
| 7,054,011 B2 | 5/2006 | Zhu et al. | |
| 7,060,965 B2 | 6/2006 | Vidovic et al. | |
| 7,149,374 B2 | 12/2006 | Lagakos et al. | |
| 2002/0159671 A1* | 10/2002 | Boyd | G01D 5/268 385/12 |
| 2003/0138185 A1 | 7/2003 | Dianov et al. | |
| 2004/0047536 A1 | 3/2004 | Pickrell et al. | |
| 2004/0067000 A1 | 4/2004 | Bates et al. | |
| 2004/0071383 A1 | 4/2004 | Balachandran et al. | |
| 2004/0077949 A1 | 4/2004 | Blofgett et al. | |
| 2004/0086228 A1 | 5/2004 | Rumpf et al. | |
| 2005/0041905 A1* | 2/2005 | Lagakos | G01L 7/086 385/12 |
| 2005/0157305 A1 | 7/2005 | Yu et al. | |
| 2005/0195402 A1 | 9/2005 | May et al. | |
| 2005/0195403 A1 | 9/2005 | Xu et al. | |
| 2005/0231729 A1 | 10/2005 | Lopushansky et al. | |
| 2005/0243308 A1 | 11/2005 | Vidovic et al. | |
| 2006/0126991 A1 | 6/2006 | Huang | |
| 2007/0006663 A1 | 1/2007 | Zerwekh et al. | |
| 2007/0147738 A1 | 6/2007 | Wang et al. | |
| 2008/0159687 A1 | 7/2008 | Donlagic et al. | |
| 2009/0202195 A1 | 8/2009 | Lagakos et al. | |
| 2009/0226128 A1* | 9/2009 | Donlagic | G01D 5/268 385/13 |
| 2009/0259150 A1 | 10/2009 | Ostrovsky et al. | |
| 2009/0279099 A1 | 11/2009 | Wang et al. | |
| 2009/0289198 A1 | 11/2009 | Youngner | |
| 2009/0320605 A1* | 12/2009 | Antila | C04B 37/005 73/718 |
| 2010/0007893 A1 | 1/2010 | Hall | |
| 2010/0058871 A1 | 3/2010 | Takeishi | |
| 2010/0135111 A1 | 6/2010 | Bates et al. | |
| 2010/0179432 A1 | 7/2010 | Thornton | |
| 2010/0206082 A1 | 8/2010 | Shimazaki | |
| 2011/0048136 A1* | 3/2011 | Birch | E21B 47/06 73/705 |
| 2012/0116255 A1 | 5/2012 | Wang et al. | |
| 2013/0319123 A1 | 12/2013 | Wang et al. | |
| 2014/0180056 A1 | 6/2014 | Hoseit | |
| 2014/0208858 A1* | 7/2014 | Jiang | G01L 11/02 73/705 |
| 2014/0270623 A1* | 9/2014 | Ahmed | G01L 11/025 385/12 |
| 2015/0141854 A1* | 5/2015 | Eberle | A61B 5/02154 600/488 |

FOREIGN PATENT DOCUMENTS

| | | |
|---|---|---|
| JP | 61191932 A | 8/1986 |
| WO | WO 94/02810 | 2/1994 |
| WO | WO 99/60341 | 11/1999 |
| WO | WO 02/23148 A1 | 3/2002 |
| WO | WO 2005/024339 A2 | 3/2005 |
| WO | WO 2007/019676 A1 | 2/2007 |
| WO | WO 2008/092372 A1 | 8/2008 |
| WO | WO 2011/008559 A1 | 1/2011 |

OTHER PUBLICATIONS

Chen, X. et al., "Deep wet etching on fused silica material for fiber optic sensors", *Proc. SPIE*, 5342: Abstract (Dec. 30, 2003).

Gander, M. J., et al., "Embedded Micromachined Fiber-Optic Fabry-Perot Pressure Sensors in Aerodynamics Applications", *IEEE Sensors Journal*, 3(1): 102-107 (Feb. 2003).

International Preliminary Report on Patentability mailed Jan. 12, 2012 of International Application No. PCT/US2010/040460, International Filing Date Jun. 29, 2009.

International Search Report and Written Opinion mailed Oct. 14, 2010 of International Application No. PCT/US2010/040460, International Filing Date Jun. 29, 2009.

Kim, Y. and Neikirk, D.P., "Micromachined Fabry-Perot cavity pressure transducer", *Photonics Technology Letters, IEEE*, 7(12): 1471-1473 (Dec. 1995).

Lee, J-R. and Tsuda, H., "A novel fiber Bragg grating acoustic emission sensor head for mechanical tests", *Scripta Materialia*, 53: 1181-1186 (2005).

Wang, W. et al., "Miniature all-silica optical fiber pressure sensor with an ultrathin uniform diaphragm", *Optics Express*, 18(9): 9006-9014 (Apr. 14, 2010).

Wang, X. et al., "An ultra-sensitive optical MEMS sensor for partial discharge detection", *Journal of Micromechanics and Microengineering*, 15: 521-527 (2005).

Xu, J. et al., "Miniature all-silica fiber optic pressure and acoustic sensors", *Optics Letters*, 30(24): 3269-3271 (Dec. 15, 2005).

NonFinal Office Action, entitled: "Photoacoustic Probe", Date Mailed Jan. 22, 2016.

Notification of the International Search Report and the Written Opinion for Int'l Application No. PCT/US2012/025646; entitled: "Photoacoustic Probe", Date Mailed: Jan. 2, 2013.

Office Action dated Jan. 22, 2016 for U.S. Appl. No. 13/984,736.

Supplementary Partial European Search Report dated Apr. 1, 2016, for International Application No. EP12746867.6 entitled "Photoacoustic Probe".

Aarabi, P., "Self-localizing dynamic microphone arrays," *IEEE Transactions on Systems. Man and Cybernetics—Part C: Applications and Reviews*, 32(4): 474-484 (2002).

Acquafresca, A., et al., "Toward Virtual Biopsy Through an All Fiber Optic Ultrasonic Miniaturized Transducer: A Proposal," *IEEE Transactions on Ultrasonics, Ferroelectrics and Frequency Control*, 50(10): 1325-1335 (2003).

Acquafresca, A., et al., "Fiber Optics Sensors for Ultrasonic Virtual Biopsy," *Proceedings of IEEE Sensors*, 1: 261-265 (2002).

Alberts, C. J., et al., "Fiber-Top Refractometer," *Measurement Science and Technology*, 20(3): 034005 (2009).

Andreev, V. G., et al., "Optoacoustic tomography of breast cancer with arc-array Transducer," *Biomedical Optoacoustics, San Jose, CA, USA*, 3916, pp. 36-47 (2000).

(56) References Cited

OTHER PUBLICATIONS

Aris, T., et al., "Optical beam steering using a liquid-crystal television panel", Microwave and Optical Technology Letters, 7(6): 285-289 (1994).
Balageas, D. L., et al., "Ultrasound generation in composites via embedded optical fiber," in Review of Progress in Quantitative Nondestructive Evaluation, D. Thompson and D. Chimenti, eds., AIP Conf., pp. 691-698 (1998).
Barrington, L., and Duffy, J., "Attracting Underrepresented Groups to Engineering With Service-Learning," Proceedings of the American Society of Engineering Education International Exposition and Conference (2007).
Beard, P. C., et al., "Optical fiber photoacoustic-photothermal probe," 23: 1235-1237 (1998).
Beard, P.C., et al., "Characterization of Post-Mortem Arterial Tissue Using Time Resolved Photoacoustic Spectroscopy at 436, 461 and 532nm," Physics in Medicine and Biology, 42: 177-198 (1997).
Beard, P.C., et al., "Comparison of a Miniature Ultrasonic Optical Fibre Hydrophone With PVDF Hydrophone Technology," in Proceedings IEEE International Ultrasonics Symposium, pp. 1881-1883 (1998).
Biagi, E., et al., "Generatore optoacustico di ultrasuoni da energia laser alimentata tramite fibra ottica", Italian, FI 2000 A 000176, International Extension Requested (2000).
Biagi, E., et al., "Photoacoustic Generation: All-Optical Fibre Transducers," in Proceedings IEEE International Ultrasonics Symposium, pp. 921-924 (1996).
Biagi, E., et al., "Photoacoustic Generation: Optical Fiber Ultrasonic Sources for Non-Destructive Evaluation and Clinical Diagnosis," Optical Review, 4(4): 481-483 (1997).
Biagi, E., et al., "All optical fiber ultrasonic sources for non destructive testing and clinical Diagnosis," Optical Sensors and Microsystems (2000).
Biagi, E., et al., "Efficient laser-ultrasound generation by using heavily absorbing films as Targets," IEEE Transactions on Ultrasonics, Ferroelectrics and Frequency Control, 48(6): 1669-1680 (2001).
Biagi, E., et al., "Fiber optic broadband ultrasonic probe," IEEE Sensors Conference, pp. 363-366 (2008).
Biagi, E., et al., "Fiber optic photoacoustic device: high efficiency and wide bandwidth ultrasonic source", IEEE Conference Proceedings, Instrumentation and Measurement Technology Conference, pp. 948-952, 1998.
Biagi, E., et al., "Guided acoustic wave propagation for porcelain coating Characterization," IEEE Transactions on Ultrasonics, Ferroelectrics and Frequency Control, 44(4): 909-916 (1997).
Biagi., E., et al., "Real Time Processing of the Radiofrequency Echo Signal for On-Line Spectral Maps," Acoustic Imaging, vol. 24: pp. 95-100 (2000).
Bobbin, "(EMAT)-High-Temperature Probe Electromagnetic Acoustic Transducer," Materials Evaluation, 37 (5): pp. 28 (1979).
Bohren, C., et al., [Absorption and Scattering of Light by Small Particles], Wiley-VCH, (2010).
Bonello, B., et al., "Application of the Picosecond Ultrasonic Technique to the Study of Elastic and Time-Resolved Thermal Properties of Materials," Ultrasonics, 35(3): 223-231 (1997).
Boonsang, S., and Dewhurst, R. J., "A Sensitive Electromagnetic Acoustic Transducer for Picometer-Scale Ultrasonic Displacement Measurements," Sensors and Actuators A: Physical, 127 (2): 345-354 (2006).
Boonsang, S., and Dewhurst, R. J., "Signal Enhancement in Rayleigh Wave Interactions Using a Laser-Ultrasound/EMAT Imaging System," Ultrasonics, 43(7): 512-523 (2005).
Bost, W., et al., "Developing a high-resolution photoacoustic microscopy platform," 4th European Conference of the International Federation for Medical and Biological Engineering, pp. 448-451 (2009).
Bowen, T., "Radiation-Induced Thermoacoustic Soft Tissue Imaging," in Proceedings IEEE International Ultrasonics Symposium, pp. 817-822 (1981).
Bretz, K. C., et al., "Picosecond Acoustics for the Characterization of Sub-Micron Polymeric Films," Ultrasonics, 34(2-5): 513-515 (1996).
Buffat, P., and Borel, J.-P., "Size effect on the melting temperature of gold particles," Physical Review A, 13(6): 2287-2298 (1976).
Buma, T., et al., "High-frequency ultrasound array element using thermoelastic expansion in an elastomeric film," Applied Physics Letters, 79(4): 548-550 (2001).
Buma, T., et al., "Thermoelastic Expansion vs. Piezoelectricity for High-Frequency, 2-D Arrays," IEEE Transactions on Ultrasonics, Ferroelectrics and Frequency Control, 50 (8): 1065-1068 (2003).
Calasso, I. G., et al., "Photoacoustic point source," Physical Review Letters, 86: 3550-3553 (2001).
Caller, R.F., et al., "Laser Ultrasound for Investigation of Arteriosclerotic Arterial Tissue," IEEE Colloquium Digest, vol. 97/124, pp. 4/1-4/6 (1997).
Carmena, J. M., et al., "The Use of Doppler in Sonar-Based Mobile Robot Navigation: Inspirations From Biology," Information Sciences, 161(1-2): 71-94 (2004).
Cassarly, W. J., et al., "Phase control of coherent diode laser arrays using liquid crystals," Proceedings SPIE, Laser Diode Technology and Applications, Luis Figueroa, Ed, pp. 130 (1989).
Cha, N.-G., et al., "Convective Assembly and Dry Transfer of Nanoparticles Using Hydrophobic/Hydrophilic Monolayer Templates," Langmuir, 25(19): 11375-11382 (2009).
Chen, Q. X., et al., "A new laser-ultrasound transducer for medical applications," Ultrasonics, 32: 309-313 (1994).
Cheng, A., et al., "Simulation of laser-generated ultrasonic waves in layered plates," Journal of the Acoustical Society of America, 110(2): 848-855 (2001).
Chiota, J., et al., "Multiscale Directed Assembly of Polymer Blends Using Chemically Functionalized Nanoscale-Patterned Templates," Small,5(24): pp. 2788-2791 (2009).
Chu, E., et al., "Intracardiac echocardiography during radiofrequency catheter ablation of cardiac arrhythmias in humans," Journal of the American College of Cardiology, 24: 1351-1357 (1994).
Cibula, E., and Donlagic, D., "Miniature fiber-optic pressure sensor with a polymer Diaphragm," Applied optics, 44(14): pp. 2736-2744 (2005).
Coleman, A.J., et al., "Acoustic Performance and Clinical Use of a Fibreoptic Hydrophone,", Ultrasound in Medicine and Biology, 24(1): 143-151 (1998).
Connor, E.E., et al., "Gold nanoparticles are taken up by human cells but do not cause acute cytotoxicity," Small, 1(3): 325-327 (Mar. 2005).
Coulette, R., et al., "Laser-generated ultrasound applied to two-layered materials characterization: Semi-analytical model and experimental validation," Ultrasonics,36: 239-243 (1998).
Crazzolara, H, et al., "Analysis of the Acoustic Response of Vascular Tissue Irradiated by an Ultraviolet Laser Pulse," Journal of Applied Physics, 70(3): 1847-1849 (1991).
Cross, F.W., et al., "Ablative and Acoustic Response of Pulsed UV Laser-Irradiated Vascular Tissue in a Liquid Environment," Journal of Applied Physics,64(4): 2194-2201 (1988).
Davies, J. P., "Surface-enhanced Raman scattering from sputter-deposited silver surfaces," Analytical Chemistry, 58: 1290-1294, (1986).
Davies, S. J., et al., "Laser-generated ultrasound: its properties, mechanisms and multifarious applications," Journal of Physics D: Applied Physics, 26(3): 329 (1993).
Dubois, M., et al., "Modeling of laser thermoelastic generation of ultrasound in an orthotropic medium," Applied Physics Letters, 64(5): 554-556 (1994).
Dutton, B., et al., "A New Magnetic Configuration for a Small In-Plane Electromagnetic Acoustic Transducer Applied to Laser-Ultrasound Measurements: Modelling and Validation," Sensors and Actuators A: Physical, 125(2): 249-259 (2006).
Dutton, B., et al., "Modeling of Magnetic Fields to Enhance the Performance of an In-plane EMAT for Laser-Generated Ultrasound," Ultrasonics, 44(Supplement 1): e657-e665 (2006).
Ebbini, E. S., and Cain, C. A., "Multiple-focus ultrasound phased-array pattern synthesis: optimal driving-signal distributions for

(56) References Cited

OTHER PUBLICATIONS hyperthermia," IEEE Transactions on Ultrasonics, Ferroelectrics and Frequency Control, 36(5): 540-548 (1989).
El-Sayed, M. A., "Some interesting properties of metals confined in time and nanometer space of different shapes," Accounts of Chemical Research, 34(4): 257-264 (2001).
Enüstün, B. V., and Turkevich, J., "Coagulation of Colloidal Gold," Journal of the American Chemical Society, 85(21): 3317-3328 (1963).
Epstein, L.M., et al., "Nonfluoroscopic transseptal catheterization: safety and efficacy of intracardiac echocardiographic guidance," Journal of Cardiovascular Electrophysiology, 9: 625-630 (1998).
Esenaliev, R. O., et al., "Studies of acoustical and shock waves in the pulsed laser ablation of biotissue," Lasers in Surgery and Medicine, 13(4): 470-484 (1993).
Eustis, S., et al., "Why Gold Nanoparticles are More Precious Than Pretty Gold: Noble Metal Surface PlasmonResonance and Its Enhancement of the Radiative and Nonradiative Poperties of Nanocrystals of Different Shapes," Chemcial Society Reviews, 35(3): 209-217 (2006).
Fan, G., and Zhiyong G., "Nano-soldering of magnetically aligned three-dimensional nanowire networks," Nanotechnology, 21(11): 115604 (2010).
Fang, Q., et al., "Effect of optical penetration on laser generated thermoelastic ultrasound in solids," Acta Acustica, 21: 165-173 (1996).
Fatemi, M., and Greenleaf, J. F., "Ultrasound-stimulated vibro-acoustic spectrography," Science, 280(5360): 82-85 (1998).
Fatemi, M., and Greenleaf, J. F., "Vibro-acoustography: An imaging modality based on ultrasound-stimulated acoustic emission," Proceedings of the National Academy of Sciences of the United States of America, pp. 6603-6608 (1999).
Federspila, Ph. A., et al., "Ultrasound-Based Navigation of Robotic Drilling at the Lateral Skull Base," InternationalCongress Series, vol. 1256: pp. 1358-1358 (2003).
Fisher, W. G., et al., "Adjunctive intracardiac echocardiography to guide slow pathway ablation in human atrioventricular nodal reentrant tachycardia: anatomic insights," Circulation, 96: 3021-3029 (1997).
Fleischman, A., et al., "Miniature High Frequency Focused Ultrasonic Transducers for Minimally Invasive Imaging Procedures," Sensors and Actuators A: Physical, 103(1-2): 76-82 (2003).
Fomitchov, P. A., et al., "Photoacoustic probes for nondestructive testing and biomedical Applications," Applied Optics, 41(22): 4451-4459 (2002).
Fomitchov, P. A., et al., "Distributed photoacoustic system for cure monitoring of Composites," Advanced Nondestructive Evaluation for Structural and Biological Health Monitoring, Newport Beach, CA, USA, 4335, pp. 323-329 (2001).
Fomitchov, P. A., et al., "Fiberized laser ultrasonic source for process monitoring and biomedical applications," Applications of Optical Fiber Sensors, Glasgow, United Kingdom, 4074, pp. 127-134 (2000).
Fomitchov, P. A., et al., "Laser ultrasonic enabled "Smart" mold for composite parts Manufacturing," Review of Progress in Quantitative Nondestructive Evaluation, Ames, Iowa, pp. 802-1807 (2001).
Foster, F.S., "Transducer Materials and Probe Construction," Ultrasound in Medicine and Biology, 26: S2-S5 (2000).
Friedman, T.L., "The World is Flat," New York: Farrar, Straud and Giroux, pp. 329 (2006).
Gao, F., et al., "Synthesis, Characterization, and Thermal Properties of Nanoscale Lead-Free Solders on Multisegmented Metal Nanowires," The Journal of Physical Chemistry C, 113(22): 9546-9552 (2009).
Ge, J., et al., "Intravascular Ultrasound Imaging of Angiographically Normal Coronary Arteries: A Prospective Study In Vivo," British Heart Journal, 71(6): 572-578 (1994).
Gibbons, M.T., "Engineering by the Numbers," http://www.asee.org/publications/profiles/upload/2008ProfileEng.pdf.

DiGiovanni, M.D., "Flat and Corrugated Diaphragm Design Handbook," Marcel Dekker (1982).
Goltsos, W., and Holz, M., "Agile beam steering using binary optics microlens arrays," Optical Engineering, 11(29): 1392-1397 (1990).
Grahn, H.T., et al., "Picosecond Ultrasonics," Journal of Quantum Electronics, 25(12): 2562-2569 (1989).
Green, D. E., et al., "The Effect of Nanoparticle-Enhanced Photoacoustic Stimulation on Multipotent Marrow Stromal Cells," ACS Nano, 3(8): 2065-2072 (2009).
Guittet, C. et al., "High-Frequency Estimation of the Ultrasonic Attenuation Coefficient Slope Obtained in Human Skin: Simulation and In Vivo Results," Ultrasound in Medicine and Biology, 25(3): 421-429 (1999).
Guthy, C.J., et al., "A Review of Temperature Measurement Methods During Twist Drilling Processes," Journal of Manufacturing Processes, (Submitted).
Haga, Y., et al., "Batch Fabrication of Intravascular Forward-Looking Ultrasonic Probe," Sensors and Actuators A: Physical,104(1): 40-43 (2003).
Handzel, A. A., and Krishnaprasad, P. S., "Biomimetic sound-source localization," IEEE Sensors Journal, 2(6): 607-616 (2002).
He, J. A., et al., "Electrostatic multilayer deposition of a gold-dendrimer nanocomposite," Chemistry of Materials, 11: 3268-3274 (1999).
http://www.enme.umd.edu/news/news_story.php?id=2612 (Miao Yu Receives AFOSR YIP Award) (retrieved from internet Aug. 22, 2014).
http://www.olympus-ims.com/en/probes (retrieved from internet Aug. 22, 2014).
http://www.ptca.org/ivus/ivus.html (Angioplasty.org, "IVUS Overview") (retrieved from internet Aug. 22, 2014).
http://www.ptca.org/news/2007/0530.html (Angioplasty.org, IVUS News, "Most Heart Stents are Placed Imperfectly, Increasing Risk of Heart Attack or Reclosure") (retrieved from internet Aug. 22, 2014).
http://www.redwoodeditor.com/content/SCAI/scai/ (On 30th Anniversary, Angioplasty Celebrated as Modern Medical Breakthrough in Stopping Heart Attack) (retrieved from internet Aug. 22, 2014).
Hua, F., et al., "Patterning of Layer-by-Layer Self-Assembled Multiple Types of Nanoparticle Thin Films by Lithographic Technique," Nano Letters, 2(11): 1219-1222 (2002).
Huang, J., et al., "Sound localization in reverberant environment based on the model of the precedence effect," IEEE Transactions on Instrumentation and Measurement, 46(4): 842-846 (1997).
Long, M., et al., "Simulation of the Path Loss for Radio Wave Propagation Based on MATLAB Language," Acta Scientiarum Naturalium UniversitatisSunyatseni, 40: 18-20 (2001).
Huang, X., et al., "Cancer cell imaging and photothermal therapy in the near-infrared region by using gold nanorods." Journal of the American Chemical Society, 128(6): 2115-2120 (2006).
Huber, F., et al., "Analyzing Refractive Index Changes and Differential Bending in Microcantilever Arrays," Review of Scientific Instruments, 79(8): 086110-3 (2008).
Huber, F., et al., "Label Free Analysis of Transcription Factors Using Microcantilever Arrays", Biosensors and Bioelectronics, 21(8):, pp. 1599-1605 (2006).
Huber, T. M., "Noncontact modal testing of hard-drive suspensions using ultrasound radiation force", Proceedings of International Modal Analysis Conference (IMAC XXIV), 2006.
Huber, T. M., et al., "Noncontact Modal Analysis of a Pipe Organ Reed Using Airborne Ultrasound Stimulated Vibrometry," Journal of the Acoustical Society of America, 119(4): 2476-2482 (2006).
Huber, T. M., et al., "Noncontact Modal Testing of Hard-Drive Suspensions Using Ultrasound Radiation Force," Journal of the Acoustical Society of America, 118: 1928 (2005).
Huber, T. M., et al., "Non-Contact Mode Excitation of Small Structures in Air Using Ultrasound Radiation Force," Journal of the Acoustical Society of America, 117(4): 2455-2455 (2005).
Huber, T.M., et al., "Mode-selective noncontact excitation of microcantilevers and microcantilever arrays in air using the ultrasound radiation force," Applied Physics Letters, 97:214101(2010).
Huber, T.M., et al., "Excitation of Vibrational Eigenstates of Coupled Microcantilevers Using Ultrasound Radiation Force," Pro-

(56) References Cited

OTHER PUBLICATIONS ceedings of the ASME 2008 International Design Engineering Technical Conferences& Computers and Information in Engineering Conference IDETC/CIE, Brooklyn, New York, USA (2008).
Hyde, J.S., and Mertz, J.E., "Gender, Culture, and Mathematics Performance," Proceedings of the National Academy of Sciences of the United States of America, pp. 8801-8807 (2009).
Iannuzzi, D., et al., "A Fiber-Top Cantilever for Hydrogen Detection," Sensors and Actuators B: Chemical, 121 (2): 706-708 (2007).
Iannuzzi, D., et al., "Fiber-Top Atomic Force Microscope," Review of Scientific Instruments, 77(10): 106105-3 (2006).
Iannuzzi, D., et al., "Monolithic Fiber-Top Sensor for Critical Environments and Standard Applications," Applied Physics Letters, 88(5): 053501 (2006).
Jackson, S., "The Quiet Crisis: Falling Short in Producing American Scientific and Technical Talent," Building Engineering and Science Talent (2002).
Jain, P. K., et al., "Calculated Absorption and Scattering Properties of Gold Nanoparticles of Different Size, Shape, and Composition: Applications in Biological Imaging and Biomedicine," The Journal of Physical Chemistry B, 110(14): 7238-7248 (2006).
Kalman, J. M., et al., "Activation and entrainment mapping defines the tricuspid annulus as the anterior barrier in typical atrial flutter," Circulation, 94: 398-406 (1996).
Kalman, J. M., et al., "In vitro quantification of radiofrequency ablation lesion size using intracardiac echocardiography in dogs," American Journal of Cardiology, 77: 217-219 (1996).
Kalman, J. M., et al., "Radiofrequency catheter modification of sinus pacemaker function guided by intracardiac echocardiography," Circulation, pp. 3070-3081 (1995).
Kalman, J. M., et al., ""Cristal tachycardias": origin of right atrial tachycardias from the crista terminalis identified by intracardiac echocardiography," Journal of the American College of Cardiology, 31: 451-459 (1998).
Kapralos, B., et al., "Audio-visual localization of multiple speakers in a video teleconferencing setting," International Journal of Imaging Systems and Technology, Special Issue on Facial Image Processing, Analysis and Synthesis, 13(1): 95-105 (2003).
Karabutov, A. A., et al., "Backward mode detection of laser-induced wideband ultrasonic transients with optoacoustic transducer," Journal of Applied Physics, 87: 2003-2014 (2000).
Kim, J.-W., et al., "Golden carbon nanotubes as multimodal photoacoustic and photothermal high-contrast molecular agents," Nat Nano, 4(10): 688-694 (2009).
Knight J., and Degertekin, L., "Capacitive Ultrasonic Transducers for Forward Looking Intravascular Imaging Arrays," In Proceedings IEEE International Ultrasonics Symposium, pp. 1052-1055 (2002).
Kopchok, G. E., et al., "Principles and Devices," Seminars in Vascular Surgery, 19(3): 128-131 (2006).
Krautkramer, J., and Krautkramer, H., "Ultrasonic testing of materials," New York: Springer Verlag (1977).
Kruger, R. A., and Liu, P., "Photoacoustic ultrasound: Pulse production and detection in 0.5% Liposyn," Medical Physics, 21(7): 1179-1184 (1994).
Lanza di Scalea, F., et al., "Remote laser generation of narrow-band surface waves through optical fibers," IEEE Transactions on Ultrasonics, Ferroelectrics and Frequency Control, 46: 1551-1557 (1999).
Lee, R. J., et al., "Radiofrequency catheter modification of the sinus node for "inappropriate" sinus tachycardia," Circulation, 92: 2919-2928 (1995).
Li, C., and Wang, L. V., "Photoacoustic tomography and sensing in biomedicine," Physics in Medicine and Biology, 54(19): R59 (2009).
Li, P., et al., "Photoacoustic flow measurements by use of laser-induced shape transitions of gold nanorods," Optics Letters,30(24): 3341-3343 (2005).

Li, X., et al., "Fabrication and Integration of Metal Oxide Nanowire Sensors Using Dielectrophoretic Assembly and Enhanced Post-assembly Processing," Sensors and Actuators B, 148: 404-412 (2010).
Lifante, G., [Integrated Photonics: fundamentals], John Wiley & Sons Ltd., England; pp. 34-37 (2003).
Lin, T. H., "Implementation and characterization of a flexure-beam micromechanical spatial light modulator," Optical Engineering, 33(11): 3643-3648 (1994).
Lin, W. C., et al., "On Dual Ultrasound Sensor Technique for Unmanned Vehicles," Automation in Construction, 1(2): 153-165 (1992).
Link, S. and El-Sayed, M. A. "Spectral properties and relaxation dynamics of surface plasmon electronic oscillations in gold and silver nanodots and nanorods," Journal of Physical Chemistry B, 103(40): 8410-8426 (1999).
Lipson, A., and Yeatman, E. M., "A 1-D photonic band gap tunable optical filter in (110) Silicon," Journal of Microelectromechanical Systems, 16(3): 521-527 (2007).
Liu, H., and Milios, E., "Acoustic positioning using multiple microphone arrays," Journal of the Acoustical Society of America, 117(5): 2772-2782 (2005).
Love, G. D., et al., "Liquid-crystal prisms for tip-tilt adaptive optics," Optics Letters, 19(15): 1170-1172 (1994).
Lu, W., et al., "Photoacoustic imaging of living mouse brain vasculature using hollow gold nanospheres," Biomaterials, 31(9): 2617-2626 (2010).
M. Han, X. Wang, J. Xu, K. L. Cooper, and A. Wang, "Diaphragm-based extrinsic Fabry-Perot interferometric optical fiber sensor for acoustic wave detection under high background pressure", Optical Engineering, vol. 44, No. 6, pp. 060506-2, 2005.
Ma, X., et al., "Surface-Enhanced Raman Scattering Sensor on an Optical Fiber Probe Fabricated by a Femtosecond Laser," Sensors, 10:11064-11071 (2010).
Maslov, K., et al., "Optical-resolution photoacoustic microscopy for in vivo imaging of single capillaries," Optics letters, 33(9): 929-931 (2008).
Masotti, L., et al., "FEMMINA—A Fast Echographic Multi-Parametric Multi-Imaging Novel Apparatus," in Proceedings IEEE International Ultrasonics Symposium, pp. 739-748 (1999).
Masotti, L., et al., "Ultrasonic Images of Tissue Local Power Spectrum by Means of Wavelet Packets for Prostate Cancer Direction," Acoustic Imaging (2002).
Matic, R. M. "Blazed phase liquid crystal beam steering", Laser Beam Propagation and Control, Los Angeles, CA, USA, pp. 194-205, 1994.
Maxfield, B. and Fortunko, C.M., "The Design and Use of EMAT's," Materials Evaluation, 41(10): S26 (1983).
Maxfield, B. W. et al., "Evaluating EMAT Designs for Selected Applications," Materials Evaluation, 45: 1166-1182 (1987).
McGee, J., et al., "In-plane indium phosphide tunable optical filter using ridge Waveguides," Semiconductor Device Research Symposium, pp. 56-57 (2005).
McLaughlan, J. R., et al., "Ultrasonic enhancement of photoacoustic emissions by nanoparticle-targeted cavitation," Optics Letters, 35(13): 2127-2129 (2010).
McRuer, R., et al., "Ferroelectric liquid-crystal digital scanner," Optics Letters, 15(23): 1415-1417 (1990).
Menichelli, D., et al., "Optoacuostic Sources: A Practical Green Function-Based Model for Thin Film Laser-Ultrasound Generation," Journal of Optics A: Pure and Applied Optics, 3(4): S23 (2001).
Metzger, C. H., and Karrai, K., "Cavity cooling of a microlever," Nature, 432(7020): 1002-1005 (2004).
Mi, B., "Implementation of fiber phased array ultrasound generation system and signal analysis for weld penetration control," In Partial Fulfillment of the Requirements for the Degree Doctor of Philosophy in School of Mechanical Engineering, Georgia Institute of Technology (2003).
Milster, T. D., and Wong, J. N., "Modeling and measurement of a micro-optic beam Deflector," Proceedings of SPIE, 1625: 78 (1992).

(56) References Cited

OTHER PUBLICATIONS

Mitchel, J. F., et al., "Intracardiac ultrasound imaging during transseptal catheterization," Chest, 108: 104-8 (1995).
Mukherjee, S., et al., "An Efficient Silver Etchant for the Fabrication of Active Nanowires Using Anodized Aluminum Oxide Templates," Electrochemical and Solid-State Letters, 13(7): D50-D52 (2010).
Murray, P. R. and Dewhurst, R. J., "A Laser/EMAT System for Thickness Monitoring Applications Using Shear and L-S Mode-Converted Waves," Measurement Science and Technology, 12: 1651-1659 (2001).
Nan Wu, Wenhui Wang, Ye Tian, Charles Guthy and Xingwei Wang, "Theoretical analysis of a novel ultrasound generator on an optical fiber tip", Proceeding of SPIE, vol. 7677, 76770X, 2010.
Nissen, S.E., et al., "Intravascular Ultrasound: Novel Pathophysiological Insights and Current Clinical Applications," Circulation, 103(4): 604-616 (2001).
Notification Concerning Transmittal of International Preliminary Report on Patentability for International Application No. PCT/US2012/025646; Date Mailed: Aug. 29, 2013.
NSF, "National Science Board Science and Engineering Indicators," Chapter. 2 (2008).
NSF, "The Engineering Workforce: Current State, Issues, and Recommendations, Final Report to the Assistant Director of Engineering," (2005).
Oksanen, M., and Wu, J., "Prediction of the temporal shape of an ultrasonic pulse in a photoacoustic sensing application," Ultrasonics, 32: 43-46 (1994).
Olgin, J. E., et al., "Electrophysiological effects of long, linear atrial lesions placed under intracardiac ultrasound guidance," Circulation, 96: 2715-2721 (1997).
Olgin, J. E., et al., "Role of right atrial endocardial structures as barriers to conduction during human type Iatrial flutter: Activation and entrainment mapping guided by intracardiac echocardiography," Circulation, 92: 1839-1848 (1995).
Olson, E. S., "Observing middle and inner ear mechanics with novel intracochlear pressure Sensors," Journal of the Acoustical Society of America, 103(6): 3445-3463 (1998).
Oraevsky, A. A., et al., "Measurement of tissue optical properties by time-resolved detection of laser-induced transient stress," Applied Optics, 36(1): 402-415 (1997).
Oralkan, O., et al., "Capacitive Micromachined Ultrasonic Transducers: Next-Generation Arrays for Acoustic Imaging?" IEEE Transactions on Ultrasonics, Ferroelectrics and Frequency Control, 49 (11): 1596-1610 (2002).
Oralkan, O., et al., "Volumetric Imaging Using 2D Capacitive Micromachined Ultrasonic Transducer Arrays (CMUTS): Initial Results", In Proceedings IEEE International Ultrasonics-Symposium, pp. 1083-1086, vol. 2., (2002).
Packer, D. L., et al., "Intracardiac phased-array imaging: methods and initial clinical experience with high resolution, under blood visualization: Initial experience with intracardiac phased-array ultrasound," Journal of the American College of Cardiology, 39 (3): 509-516 (2002).
Petrova, H., et al., "Photothermal Properties of Gold Nanoparticles," Zeitschrift für Physikalische Chemie, 221(3): 361-376 (2007).
Reid, G. L., and Milios, E., "Active stereo sound location," Journal of the Acoustical Society of America, 113: 185-193 (2003).
Ren, J. F., et al., "Intracardiac catheter echocardiographic (9MHz) imaging: in vivo validation and initial clinical applications (abstr)," Journal of the American Society of Echocardiography, 10: 406 (1997).
Resler, D. P., et al., "High-efficiency liquid-crystal optical phased-array beam steering," Optics Letters, 21(9): 689-691 (1996).
Reverdy, F., and Audoin, B., "Ultrasonic measurement of elastic constants of anisotropic materials with laser source and laser receiver focused on the same interface," Journal of Applied Physics, 90(9): 4829-4835 (2001).

Roome, K. A., et al., "Towards a Sideways Looking Intravascular Laser-Ultrasound Probe," Sensors and Actuators A: Physical, 76(1-3): 197-202 (1999).
Royer, D., and Dieulesaint, E., "Influence of the elastic properties of the backing material in thermoelastic wave generation," in Proceedings IEEE International Ultrasonics Symposium, pp. 664-667 (1983).
Saadany, B., et al., "Free-space tunable and drop optical filters using vertical Bragg mirrors on silicon," IEEE Journal of Selected Topics in Quantum Electronics, 12(6): 1480-1488 (2006).
Said, A. A., et al., "Carving Fiber-Top Cantilevers With Femtosecond Laser Micromachining," Journal of Micromechanics and Microengineering, 18(3): 035005 (2008).
Sassaroli, E., et al., "Numerical investigation of heating of a gold nanoparticle and the surrounding microenvironment by nanosecond laser pulses for nanomedicine applications," Physics in Medicine and Biology, 54: 5541-5560 (2009).
Savateeva, E. V., et al., "Noninvasive detection and staging of oral cancer in vivo with confocal optoacoustic tomography," Biomedical Optoacoustics, San Jose, CA, USA, 3916, pp. 55-66 (2000).
Schulz, L.G., "The Optical Constants of Silver, Gold, Copper and Aluminum. I. The Absorption Coefficient k," J. Opt. Soc. Am., 44(5); 357-362 (1954).
Schulz, L.G., et al., "Optical Constants of Silver, Gold, Copper and Aluminum. II. The Index of Refraction n," J. Opt. Soc. Am., 44(5); 362-367 (1954).
Schwartz, S. L., et al., "Intracardiac echocardiography in humans using a small-sized (6F), low frequency (12.5 MHz) ultrasound catheter: Methods, imaging planes and clinical experience," Journal of the American College of Cardiology, 21: 189-198 (1993).
Scruby, C. B., and Drain, L. E., "Laser ultrasonics: Techniques and applications," Hilger, New York (1990).
Sharp, G., and Johnson, K., "High speed analog complex-amplitude liquid crystal light Modulator," Optics Letters, 19(16) 1994.
Shinn-Cunningham, B., "Localizing sound in rooms," Proceedings of the ACM Siggraph and Eurographics Campfire: Acoustic Rendering for Virtual Environments, Snowbird, Utah, pp. 17-22 (2001).
Skolnik, M. I., "Introduction to Radar Systems," (N.Y: McGraw-Hill) (1962).
Smith, K., et al., "Fiber-Top Atomic Force Microscope: A Worthwhile Challenge," Opto-Electronics and Communications Conference, 2008 and the 2008 Australian Conference on Optical Fibre Technology, pp. 1-4 (2008).
Spencer, T., et al., "Characterization of Atherosclerotic Plaque by Spectral Analysis of Intravascular Ultrasound: An Invitro Methodology," Ultrasound in Medicine and Biology, 23(2): 191-203 (1997).
Stearns, R. G., and Kino G. S., "Effect of electronic strain on photoacoustic generation in Silicon," Applied Physics Letters, 47(10): 1048-1050 (1985).
Stievater, T. H., et al., "All-optical micromechanical chemical sensors," Applied Physics Letters, 89(9): 091125-3 (2006).
Sun et al., "Simulation on photoacoustic conversion efficiency of optical fiber-based ultrasound generator using different absorbing film materials" SPIE Smart Structures/NDE (2011).
Sun, K., et al., "Finite Element Modeling of an Optical Fiber Photoacoustic Generator Performance," SPIE Smart Structures/NDE, (2011).
Swift, C. I., et al., "Laser generated ultrasound using directly coated fibre optic Patchcords," Electronics Letters, 36(25): pp. 2113-2114 (2000).
Tam, A. C., "Applications of photoacoustic sensing techniques", Reviews of Modern Physics, 58(2): 381 (1986).
Telschow, K. L., and Conant, R. J., "Optical and thermal parameter effects on laser-generated ultrasound," Journal of the Acoustical Society of America, 88: 1494-1502 (1990).
Thompson, R. B., "New EMAT Configuration for Generating Sh-Waves in Ferromagnetic Materials," IEEE Transactions on Sonics and Ultrasonics, 26(2): 149 (1979).
Timoshenko, S., and Goodier, J., "Theory of elasticity," (NY: McGraw-Hill) (1970).

(56) References Cited

OTHER PUBLICATIONS

Totsu, K., et al., "Ultra-miniature fiber-optic pressure sensor using white light Interferometry," Journal of Micromechanics and Microengineering, 15: 71-75 (2005).
Tung, T.L., et al., "Source localization and spatial filtering using wideband music and maximum power beamforming for multimedia applications," IEEE Workshop on Signal Processing Systems, pp. 625-634 (1999).
Udd, E., "Fiber optic sensors: An introduction for engineers and scientists," NY: John Wiley & Son, Inc. (1990).
Vakarelski, I. U., et al., "Thermal modification of layer-by-layer assembled gold nanoparticle films," Colloids and Surfaces A:Physicochemical and Engineering Aspects, 340(1-3): 193-198 (2009).
Viadero, D., "Researchers Mull STEM Gender Gap," Published Online: http://www.edweek.org/ew/index.html, 2009.
Vogel, J. A.., et al., "Beamsteering of laser generated ultrasound," Proceedings of Ultrasonics International, Butterworth, Washington, D. C., pp. 141-152 (1987).
Von Gutfeld, R. J., "Thermoelastic generation of elastic waves for non-destructive testing and medical applications," Ultrasonics, 18: 175-181 (1980).
Von Gutfeld, R. J., "Thermoelastically Generated MHz Elastic Waves from Constrained Surfaces," in Proceedings IEEE International Ultrasonics Symposium, pp. 397-402 (1977).
Von Gutfeld, R. J., and Melcher, R. L., "20-MHz acoustic waves from pulsed thermoelastic expansions of constrained surfaces," Applied Physics Letters, 33: 175-181 (1980).
Wang, L. V., "Prospects of photoacoustic tomography," Medical Physics, 35(12): 5758-5767 (2008).
Wang, W., and Wang, X., "Label-Free Fiber Optic Biosensor With Single PMMA Functional Layer," International Conference on Optical Fibre Sensors, Western Australia, (2008).
Wang, W., et al., "Optical Interferometric Biosensor With PMMA as Functional Layer," Fall Meeting of Material Research Society, Boston, 1133-AA03-02 (2008).
Wang, W., et al., "Surface-enhanced Raman scattering on optical material fabricated by femtosecond laser," Proceeding of SPIE, Defense, Security, and Sensing, Orlando, FL, USA (Apr. 5-9, 2010).
Wang, W., et al., "Surface-enhanced-raman-scattering on quartz substrate and optical fiber with nanostructures fabricated by femtosecond laser," Fall meeting of Material Research Society, Boston (2008).
Wang, W., et al., "Fabry-Perot Type Optical Fiber Pressure/Acoustic Sensor With Accurate Cavity Length Control," The 7th International Workshop on Structural Health Monitoring 2009, Stanford University, Stanford, CA (2009).
Wang, X., and Li, D., "Comparison of IC-Engine Pressure Sensor Technologies and Their Prospects," Diesel Engine, pp. 20-33 (2003).
Wang, X., et al., "Diaphragm design guidelines and an optical pressure sensor based on MEMS technique," Microelectronics Journal, 37(1): 50-56, 1, (2006).
Wang, X., et al., "Implementation of Nondestructive Young's Modulus Measurement by Miniature Optical Sensors," SPIE OpticsEast—Sensors for Harsh Environments, Boston, MA, 5998, 599805 (2005).
Wang, X, et al., "All-fused-silica miniature optical fiber tip pressure sensor," Optics Letters, 31(7): 885-887 (2006).
Wang, X., et al., "An optical fiber tip pressure sensor for medical applications," Quantum Electronics and Laser Science Conference, pp. 916-918 (2005).
Wang, X., et al., "Label-Free DNA Detection on the Surface of an Optical Fiber Tip," Conference on Lasers and Electro-Optics/Quantum Electronics and Laser Science Conference (CLEO/QELS), Long Beach, CA, pp. CMR3 (2006).
Wang, X., et al., "Miniature Optical Fiber Sensor for Dynamic Pressure Measurements Under High Background Pressure," Optics and Photonics, San Diego, CA (2006).
Wang, X., et al., "Noninvasive laser-induced photoacoustic tomography for structural and functional in vivo imaging of the brain," Nature Biotechnology, 21(7): 803-806 (2003).
Wang, X., et al., "Study on the layer-by-layer electrostatic self assembly method for biomolecule immobilization onto biosensor surface," Nanocoatings, San Diego, CA, USA, 6647, 66470G-9 (2007).
Wang, X., et al., "Verifying an All Fused Silica Miniature Optical Fiber Tip Pressure Sensor Performance With Turbine Engine Field Test," SPIE OpticsEast—Sensors for Harsh Environments, Boston, MA, pp. 23-26 (2005).
Wang, Z., et al., "Optical High DC Voltage Sensor Based on White-Light Interferometry," IEEE Photonics Technology Letters, 18 (19): 2002-2004 (2006).
Wang, Z., et al., "Frequency-Division Multiplexed Fiber Fabry-Perot Interferometric Sensor Based on Wideband Bragg Gratings," IEEE Photonics Technology Letters,19 (8): 622-624 (2007).
Watson, E. A., "Analysis of beam steering with decentered microlens arrays," Optical Engineering, 32: 2665-2670 (1993).
Watson, R. J., et al., "Classification of Arterial Plaque by Spectral Analysis of In Vitro Radio Frequency Intravascular Ultrasound Data,"Ultrasound in Medicine and Biology, 26 (1): 73-80 (2000).
Wei, M., et al., "Directed Assembly of Polymer Blends Using Nanopatterned Templates," Advanced Materials, 21(7): 794-798 (2009).
Wei, M., et al., "Fabrication of Patterned Conducting Polymers on Insulating Polymeric Substrates by Electric-Field-Assisted Assembly and Pattern Transfer," Macromolecular Rapid Communications, 27(21): 1826-1832 (2006).
Wetsel, G. C., "Photothermal generation of thermoelastic waves in composite media," IEEE Transactions on Ultrasonics, Ferroelectrics and Frequency Control, 33(5): 450-461 (1986).
Wetsel, G., "Thermoelastic wave generation by the heated interface between two media," in Proceedings IEEE International Ultrasonics Symposium, pp. 645-648 (1980).
White, R. M., "Generation of elastic waves by transient surface heating," Journal of Applied Physics, 34(12): 3559-3567 (1963).
Wilkens, V., and Koch, C., "Fiber-optic multilayer hydrophone for ultrasonic Measurement," Ultrasonics, 37(1): 45-49 (1999).
Wu, N., et al., "Fiber Optics Photoacoustic Generation Using Gold Nanoparticles as Target," SPIE Smart Structures/NDE, (2011).
Wu, S. T., "Room temperature diphenyl-diacetylene liquid crystals," Applied Physics Letters, 61: 630 (1992).
Wu, S. T., and Wu, C. S., "Experimental confirmation of the Osipov-Terentjev theory on the viscosity of nematic liquid crystals," Physical Review Letters, 42(4): 2219-2227 (1990).
Wu, S. T., et al., "Physical properties of diphenyl-diacetylenic liquid crystals," Journal of Applied Physics, 65: 4372 (1989).
Xu, J., et al., "High-Temperature Thermometer With Fiber Optic Readout," SPIE OpticsEast—Sensors for Harsh Environments, Boston, MA, 5998, 59980B (2005).
Xu, J., et al., "Vacuum-Sealed High Temperature High Bandwidth Fiber Optic Pressure and Acoustic Sensors," SPIE OpticsEast—Sensors for Harsh Environments, Boston, MA, 5998, 599809 (2005).
Xu, J., et al., "A Novel Temperature-Insensitive Optical Fiber Pressure Sensor for Harsh Environments," IEEE Photonics Technology Letters, 17(4): 870-872 (2005).
Xu, J., et al., "Epoxy-Free High Temperature Fiber Optic Pressure Sensors for Gas Turbine Engine Applications," SPIE OpticsEast—Sensors for Harsh Environments, Philadelphia, PA: pp. 1-10 (2004).
Xu, J., et al., "Miniature All-Silica Fiber Optic Pressure and Acoustic Sensors," Optics Letters, 30 (24): 3269-3271 (2005).
Xu, J., et al., "Miniature Fiber Optic Pressure and Temperature Sensors," SPIE OpticsEast—Sensors for Harsh Environments, Boston, MA, 6004, 600403 (2005).
Xu, J., et al., "Miniature Temperature-Insensitive Fabry-Perot Fiber-Optic Pressure Sensor," IEEE Photonics Technology Letters, 18(10): 1134-1336 (2006).
Xu, L., et al., "Noncovalent Nonspecific Functionalization and Solubilization of Multi-Walled Carbon Nanotubes at High Concentrations with a Hyperbranched Polyethylene," Macromolecular Chemistry and Physics, 210(24): 2194-2202 (2009).

(56) References Cited

OTHER PUBLICATIONS

Xu, M., and Wang, L.V., "Analytic explanation of spatial resolution related to bandwith and detector aperture size in thermoacoustic or photoacoustic reconstrcution," Physcial Review E, 67(5) 056605 (2003).

Yang, X., et al., "Nanoparticles for photoacoustic imaging," Wiley Interdisciplinary Reviews: Nanomedicine and Nanobiotechnology, 1(4): 360-368 (2009).

Yock, P.G., et al., "Intravascular Ultrasound: State of the Art and Future Directions," The American Journal of Cardiology, 81 (7, Supplement 1): 27E-32E (1998).

York, E. A., "Gender Differences in the College and Career Aspirations of High School Valedictorians," Journal of Advanced Academics, 19: 578-600 (2008).

Yu, M., "Biology-inspired miniature optical directional microphones: Bridging biological systems and sensor technology," NSF Program(s): Sensors and sensing systems, Award Abstract #: 0644914 (2007).

Yu, M., and Balachandran, B., "Acoustic measurements using a fiber optic sensor system," Journal of Intelligent Material Systems and Structures, 14(7): 409-414 (2003).

Zhang, H. F., et al., Imaging of Hemoglobin Oxygen Saturation Variations in Single Vessels In Vivo Using Photoacoustic Mircoscopy, Applied Physics Letters, 90(5): 053901-N.PAG (2007).

Zhang, H.F., et al., "In vivo imaging of subcutaneous structures using functional photoacoustic microscopy," Nature Protocols, 2(4): 797-804 (2007).

Zhang, H.F., et al., "Functional photoacoustic microscopy for high-resolution and noninvasive imaging," National Biotechnology, 24(7): 848-51 (2006).

Zharov, V. P., et al., "Photothermal detection of local thermal effects during selective nanophotothermolysis," Applied Physics Letters, 83(24): 4897-4899 (2003).

Zhou, S., et al., "Finite-element analysis of material and parameter effects in laser-based thermoelastic ultrasound generation," IEEE Transactions on Ultrasonics, Ferroelectrics and Frequency Control, 51(9): 1178-1186 (2004).

Zhu, Y., et al., "Miniaturized Fiber Optic High-Temperature Pressure Sensor," SPIE OpticsEast—Sensors for Harsh Environments, Philadelphia, PA: pp. 11-18 (2004).

Extended European Search Report, "Photoacoustic Probe," date of mailing Aug. 16, 2016.

Notice of Allowance and Fees Due, "Photoacoustic Probe," date of mailing Aug. 18, 2016.

Notice of Allowance and Fees Due for U.S. Appl. No. 13/984,736, entitled: "Photoacoustic Probe," date of mailing Oct. 26, 2016.

\* cited by examiner

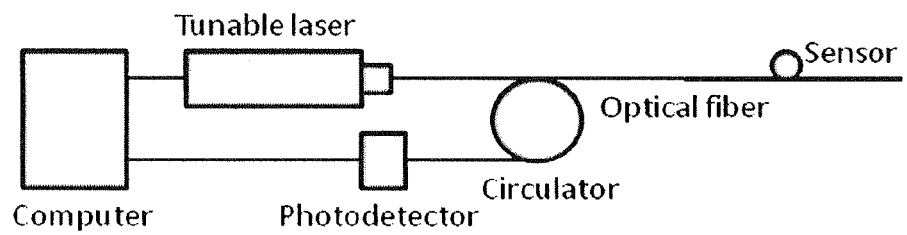
Figure 17
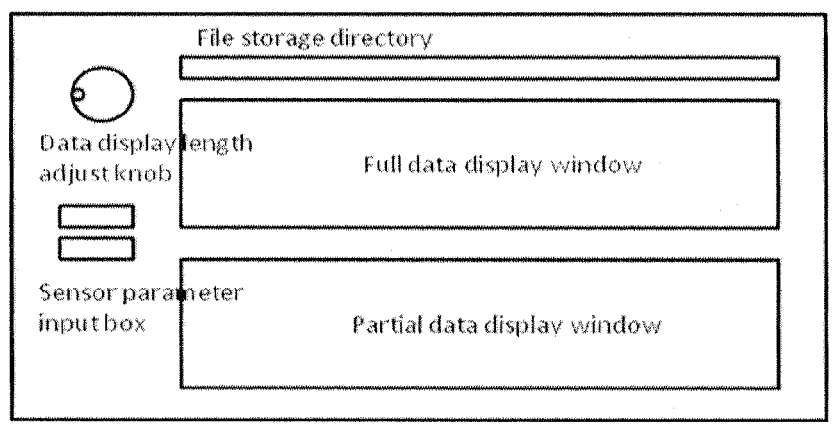
Figure 18. The user interface of the Labview™ program controlling the laser and spectrum collection.
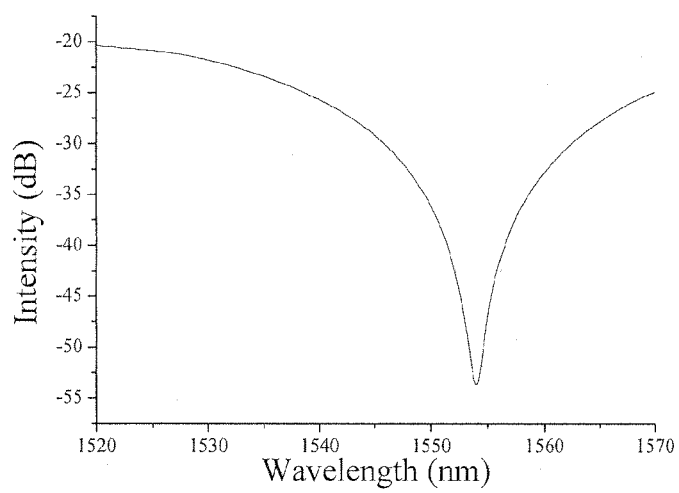
Figure 19. UML fiber sensor reflection spectrum collected in the CEMOS lab.

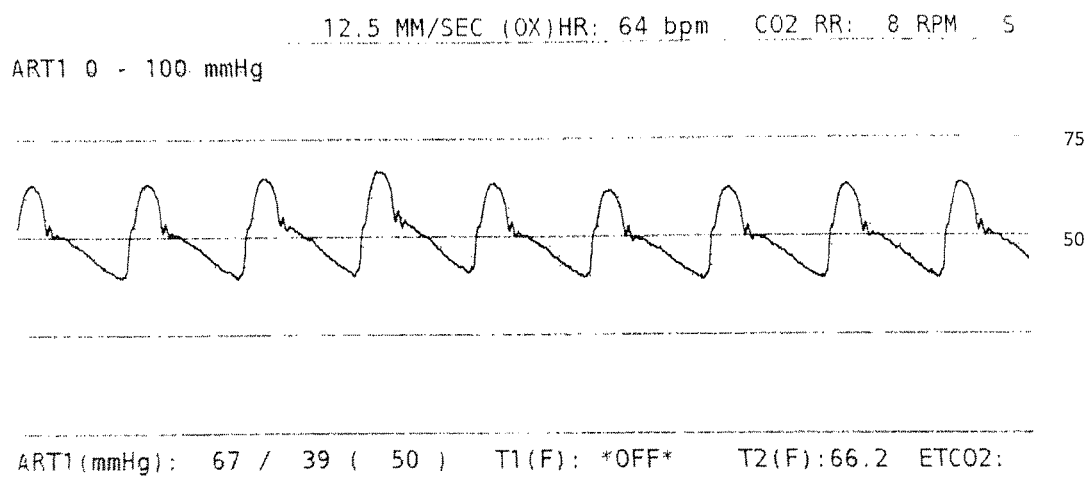
Figure 20. The blood pressure waveform measured by the hospital catheter transducer.
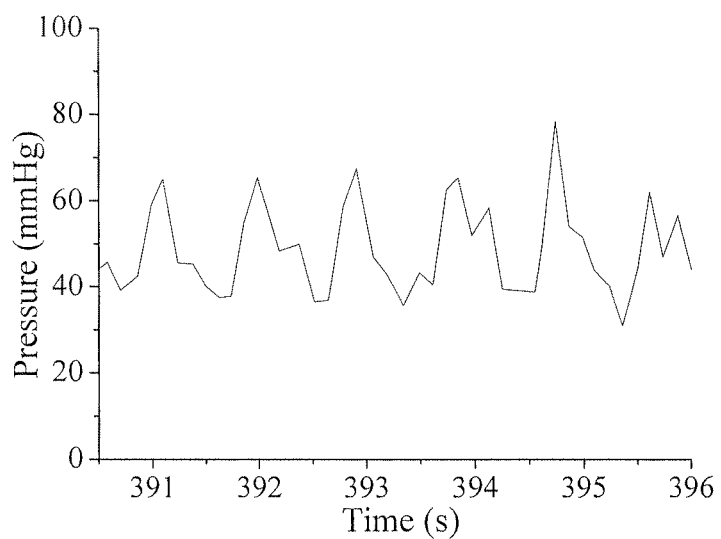
Figure 21. The blood pressure waveform from the optical BP sensor.

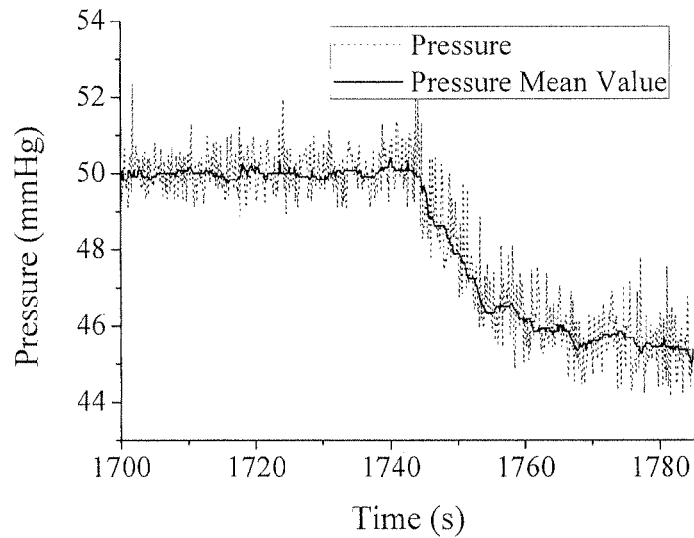
Figure 22. Pressure measured by UML pressure sensor decreased from 50 mmHg to 45 mmHg, caused by complete occlusion of coronary vessel.
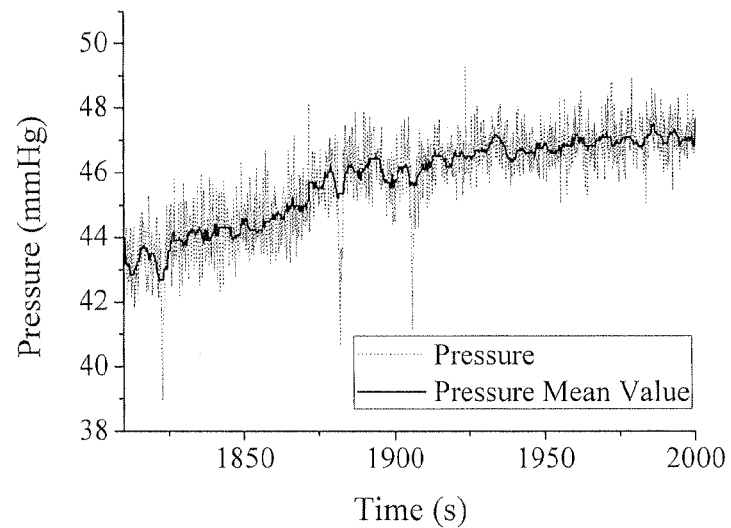
Figure 23. Blood pressure measured by UML sensor increased gradually following partial deflation with resolution of the occlusion.

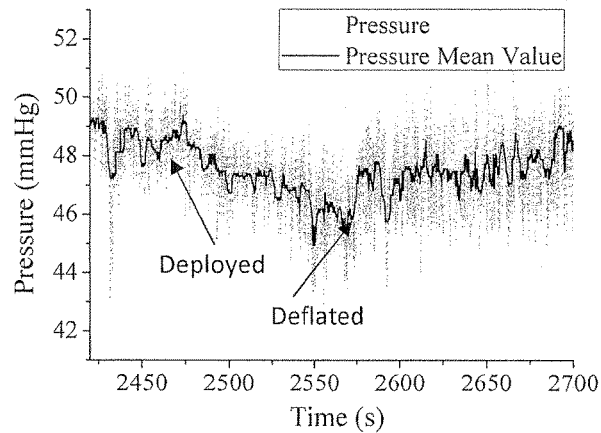

(a)

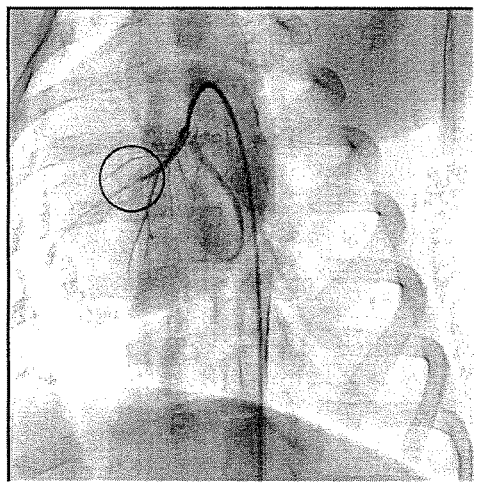

(b)

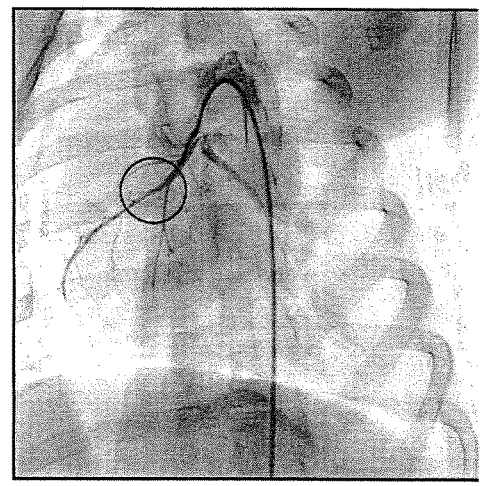

(c)

Figure 24. (a) The pressures measured by UML sensors decreased then increased due to deployment and deflation of the coronary occluder. (b) Coronary angiography following introduction of the UML fiber pressure sensor into the LAD. The circle identifies a 90% stenosis with markedly reduced flow at the site of the vascular occluder. (c) Angiography demonstrates alleviation of the critical stenosis following deflation of the vascular occluder.

OPTICAL FIBER PRESSURE SENSOR WITH UNIFORM DIAPHRAGM AND METHOD OF FABRICATING SAME

RELATED APPLICATION

This application is the U.S. National Stage of International Application No. PCT/US2010/040460, filed Jun. 29, 2010, which designates the U.S., published in English, and claims the benefit of U.S. Provisional Application No. 61/221,429, filed Jun. 29, 2009. The entire teachings of the above applications are incorporated herein by reference.

BACKGROUND OF THE INVENTION

Optical fiber sensors that use Fabry-Perot cavities to detect pressure and/or temperature are very sensitive and compact. Typical optical fiber sensors include a cavity formed by a diaphragm or a cavity assembly on the end of an optical fiber. Light transmitted through the fiber reflects off both the end of the fiber and the diaphragm, creating a signal that varies with the cavity length, which changes with temperature and pressure. Usually, the thinner the diaphragm, the more sensitive the cavity. The uniformity of the diaphragm thickness is also important; if the thickness varies too much, then the sensor may produce unpredictable, unrepeatable measurements.

Optical fiber sensors are small and their geometrical flexibility make them easy to connect to current tools and to use in small or restricted spaces. Optical fiber sensors generally are immune to electromagnetic interference, inert to chemical erosion, and insensitive to thermal variations. In addition, optical fiber sensors can survive in high-pressure, high-temperature cure cycle environments, such as those encountered during structure fabrication, system integration, and daily use.

Micro Fabry-Perot cavities may be fabricated using a combination of surface micromachining technology. (See, e.g., Y. Kim and D. P. Neikirk, "Micromachined Fabry-Perot Cavity Pressure Transducer," IEEE Phot. Technol. Letters, 7: 1471-1473, 1995, incorporated herein by reference in its entirety.) Micromachined cavities exhibit good repeatability and can be made with well-controlled cavity lengths. Micromachined cavities typically have limited cavity lengths, however, due to the nature of the surface micromachining process; reported lengths are 0.6 µm and 1.6 µm, which may not be useful in every application. In addition, fluctuations in temperature can cause different layers of the micromachined cavities to change cavity length (i.e., thickness or shape of the diaphragm), affecting measurement accuracy. Also, fabrication techniques may result in a lack of uniformity inside or between wafers. Micromachined cavities are also difficult to integrate with optical fiber due to the complexity of the cavity (sensor) assemblies.

Bulk-micromachining cavities on wafers can make both fabrication and the resulting device structures simpler. Though fiber sensors with bulk-micromachined cavities may be easier to assemble and more accurate than surface-micromachined cavities, the uniformity of the cavity length in bulk-micromachined cavities is difficult to control because the wafer thickness can vary and the fabrication process can be non-uniform.

Moreover, fiber sensors with micromachined cavities must be assembled by fixing the cavities to the fibers with glue or epoxy, which requires extremely precise alignment. The cavities are usually larger than the optical fibers, so the sensors tend to be fragile. In addition, the glue or epoxy may not hold at high temperatures or pressures; worse, the glue or epoxy may shrink or expand at a different rate than the surrounding material, degrading the sensor's temperature stability.

To avoid problems with glue or epoxy, the sensor head can be bonded directly to the optical fiber with one of a variety of bonding techniques. For example, a sensor can be made by coating a thin film with a polyimide spacer, then bonding the surface coated with polyimide spacer to the end face of an optical fiber to form a cavity. Unfortunately, polyimide's properties depend greatly on temperature, so polyimide-based sensors are not suitable for use in harsh environments.

Sensors made using laser fusion bonding use ferrules instead of polyimide to connect thin fused-silica diaphragms to optical fibers. The diaphragms are connected to a ferrule, which is then bonded to an optical fiber. Ferrule-based devices have wide working temperature ranges plus outstanding temperature stability. They are bulky, however, and the diaphragms tend to be too thick for applications that require high sensitivity. In addition, the cavity length is difficult to control during mass production.

Splicing is a well-known way to bond together pairs of optical fibers that can also be used to bond a fused silica diaphragm to the end of an optical fiber. Splice-bonded sensors are compact—the silica diaphragm has a diameter equal to that of the optical fiber and exhibit outstanding thermal performance. With splicing, though, it is still difficult to control the thickness of the diaphragm and the cavity length. Typically, spliced sensors are made by splicing a fiber with a flat end to a fiber that has been partially etched away. One of the fibers is cut away with a cleaver, leaving a relatively thick (e.g., 3-6 µm) diaphragm that can be wet-etched, if desired, to create a thinner diaphragm. Unfortunately, cleaving tends to leave a non-uniform diaphragm, and the wet etching used to reduce the diaphragm thickness also tends to result in non-uniform thickness. Moreover, it is extremely difficult to splice the bonded fiber thin enough to form a diaphragm that is less than about 3 µm thick. Repeatability is also a problem because spliced sensors are fabricated individually.

Anodic bonding is another well-known bonding technique that can be used to bond silicon to glass. Usually, the fiber end face is etched using photolithography, then a thin silicon film is bonded directly to the etched end face. Anodic bonding has the following drawbacks: (1) the fiber tip must be large enough to handle during photolithography, e.g., 200 µm or more in diameter; (2) the fiber tip must be coated with silver during photolithography, increasing the fabrication cost; (3) anodic bonding between silicon and glass fibers requires that the fiber be specially doped with alkali ions, such as $Na^+$, $La^+$, or $K^+$; (4) anodically bonded sensors have poor sensitivity because the silicon diaphragm is usually 3-10 µm thick; and (5) the diaphragm and the fiber are made of different materials, so thermal stability is still an issue.

Therefore, there is a need for a miniature optical fiber pressure sensor and a method for making such a sensor that overcomes or substantially reduces the above-mentioned problems.

SUMMARY OF THE INVENTION

Embodiments of the present invention include a sensor that comprises a silica, silicon oxide, or silica nitride diaphragm in contact with an optical fiber such that a cavity is defined by a surface of the optical fiber and a surface of the diaphragm. The surface of the optical fiber can oppose the surface of the diaphragm, whose thickness varies by between about 1% and about 10%, or, more preferably, by up to and including about 5%. In one embodiment, the surfaces are plane parallel to each other.

In certain embodiments, the optical fiber includes a core aligned along a major axis of the optical fiber and a cladding disposed radially over at least a portion of the core. The surface of the optical fiber can include a surface of the core essentially normal to the major axis of the optical fiber. The surface of the diaphragm can be in contact with the cladding. At least a portion of the surface of the optical fiber can be recessed within the optical fiber. Similarly, at least a portion of the surface of the diaphragm can be recessed within the diaphragm.

In other embodiments, the optical fiber and the diaphragm each include materials with essentially nominal coefficients of thermal expansion. Example diaphragm materials include silica (silicon dioxide), silicon, silicon nitride, and/or silicon monoxide. Preferably, the diaphragm is fabricated as a film, such as a silica thin film, on a silicon substrate and released from the substrate using etching wet etching and dry etching are suitable, although dry etching, such as deep reactive ion etching, is preferred—before or after the diaphragm is bonded to the optical fiber. The diaphragm thickness is approximately equal to the thickness of the film deposited on the substrate and can be 0.05-10 microns in thickness; more preferably, the diaphragm has a thickness equal to or less than about one micron, 0.75 micron, or 100 nm.

Embodiments of the present invention also include a method of making a sensor by placing a thin film in direct contact with an optical fiber to define a cavity between a surface of the optical fiber and a surface of the thin film. Heating either the thin film, the optical fiber, or both the thin film and the optical fiber causes the thin film to bond to the optical fiber, forming a cavity bounded by the optical fiber on one side and a thin-film diaphragm on the other. For example, silica thin films can be heated to about 200 degrees Celsius or higher for bonding to silica fibers, whereas silicon thin films are often heated to at least about 700 degrees Celsius for bonding to silica fibers. The thin film is released from a substrate, before or after heating, with wet or dry etching.

Example methods can further include the step of forming a recess in the surface of the optical fiber before bonding the thin film to the optical fiber, possibly by removing part of a core of the optical fiber. Alternatively (or in addition), a recess can be formed in the surface of the thin film before bonding the thin film to the optical fiber.

In some embodiments, bonding the thin film to the optical fiber includes simultaneously heating the thin film and the optical fiber at the same time, thereby causing the thin film to bond to the optical fiber. Bonding can be performed by illuminating the surface of the thin film with a laser beam. During heating, the length of the cavity can be adjusted by pushing or pulling on the thin film or the optical fiber. For example, the cavity length can be adjusted during heating to ensure operation in the linear regime to improve signal quality.

Still further embodiments of the present invention include a method of sensing pressure with the optical fiber sensors described above. An optical beam is transmitted to an optical fiber sensor that includes a cavity defined by an optical fiber and a diaphragm with a uniform thickness. Reflections from surfaces of the cavity, including at least one surface of the diaphragm, produce an interference pattern whose intensity and phase are indicative of pressure exerted on the cavity.

Because the diaphragm has a uniform thickness, it performs more consistently than other sensors. In addition, the use of a silica thin film diaphragm made by deep reactive ion etching enables greater sensitivity because the diaphragm can be very thin (e.g., about 50-750 nm thick). Alternatively, the sensor can be made with thicker diaphragms (e.g., 10 µm thick films) to withstand higher pressures. A sensor with a silica diaphragm in direct contact with an optical fiber is also less susceptible to error induced by temperature fluctuations caused by differences in expansion and contraction rates from that of an optical fiber with which it is in contact. At the same time, due to the outstanding chemical resistance and biocompatibility of silica, the sensor can be used in applications as diverse as monitoring in harsh environments and cardiovascular blood pressure monitoring.

The fabrication process is relatively straightforward and the fabrication parameters can be well-controlled, leading to low cost and good repeatability. For example, substrates with isolated silicon islands enable batch processing for diaphragm release, typically resulting in even lower manufacturing cost and better uniformity. In addition, the cavity length can be monitored and adjusted during fabrication, possibly to ensure operation in a linear regime.

Optical fiber sensors of the invention can be used for a variety of applications that require high sensitivity and fine resolution for measurement of pressure in tight spaces. For example, optical fiber sensors can be integrated into catheters and used to measure blood pressure intravenously or in arteries during angioplasties. They can also be embedded in other catheters for pressure measurement in the brain, lungs, or bladder. Optical fiber sensors can also be used for remote sensing in industrial applications, such as down-hole oil well pressure measurement.

BRIEF DESCRIPTION OF THE DRAWINGS

FIG. 17 is schematic diagram of an experimental setup used to measure blood pressure in a pig study conducted at the CEMOS lab.

FIG. 18 illustrates the user interface of the Labview™ program controlling the laser and spectrum collection by the setup shown in FIG. 17.

FIG. 19 is a plot of the fiber sensor reflection spectrum collected in the CEMOS lab.

FIG. 20 is a plot of the blood pressure waveform measured by a hospital catheter transducer.

FIG. 21 is a plot of the blood pressure waveform from the optical fiber sensor shown in FIG. 17.

FIG. 22 is a plot of pressure measured by the optical fiber sensor of FIG. 17 showing a decrease in blood pressure from 50 mmHg to 45 mmHg, caused by complete occlusion of coronary vessel.

FIG. 23 is a plot of blood pressure measured by the optical fiber sensor of FIG. 17 showing a gradual increase in blood pressure following partial deflation with resolution of the occlusion.

FIG. 24 includes (a) a plot of pressure measured by the optical fiber sensor of FIG. 17 showing that the pressure decreased then increased due to deployment and deflation of the coronary occluder; (b) a coronary angiogram following introduction of the UML fiber pressure sensor into the left anterior descending coronary artery with a circle that identifies a 90% stenosis with markedly reduced flow at the site of the vascular occluder; and (c) another angiogram showing alleviation of the critical stenosis following deflation of the vascular occluder.

DETAILED DESCRIPTION OF THE INVENTION

Figure 1A:
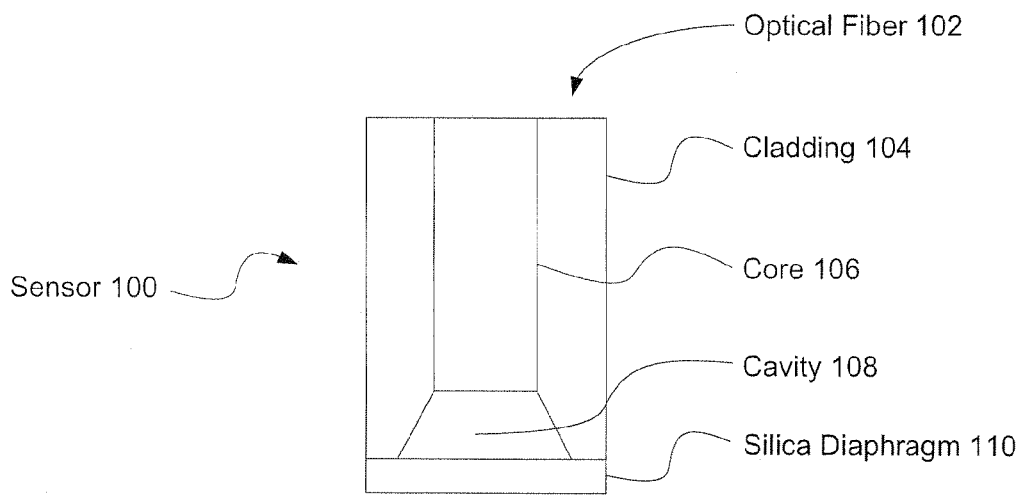
FIGS. 1A-1C are schematic illustrations of fiber sensors according to different embodiments of the present invention.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

In one embodiment, the optical pressure sensor of the invention includes a silica thin film contacting an optical fiber. The optical pressure sensor can be fabricated by employing, for example, localized or confined heating methods, including, for example, laser heating, electrode discharge heating and flame heating. Depending on the heating method, the cavity formed between the silica thin film and the optical fiber can be evacuated or filled with fluid, such as inert gas. The thin film can be fixed on a solid substrate during bonding and released after bonding, resulting in a sensor whose diameter can be the same as the diameter of the optical fiber (e.g., 125 µm for single-mode fiber). In addition, the solid substrate can be patterned or made into an array with MEMS technology.

Optical Fiber Sensors

Figure 1B:
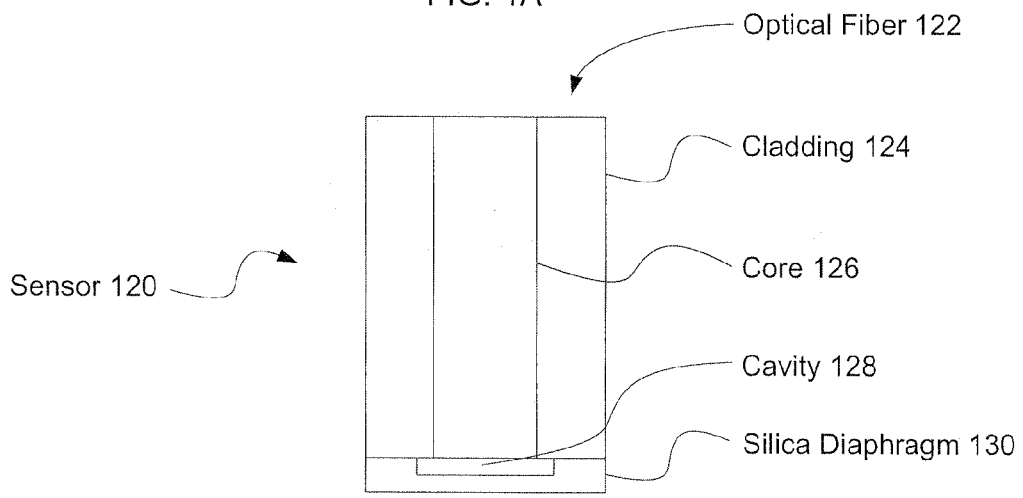
Figure 1C:
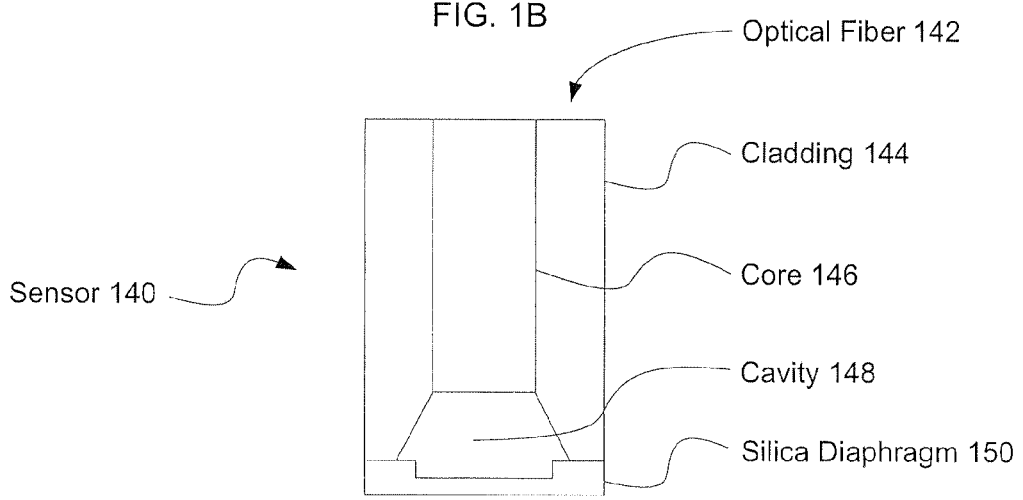

FIGS. 1A-1C show different versions of the present inventive optical fiber sensor. FIG. 1A shows the profile of a sensor 100 made of optical fiber 102 with a core 106 surrounded by a cladding 104. The difference in refractive indices between the core 106 and the cladding 104 allows the fiber 102 to guide light over long distances with very low loss in one or more modes; depending on the embodiment, the fiber 102 may be either single-mode fiber or multimode fiber as determined, in part, by the diameter of the core 106. Part of the core 106 is etched away to form a recess in the fiber 102. A silica diaphragm 110 in contact with the cladding 104 defines a cavity 108 between the recess in the fiber 102 and the diaphragm 110.

The diaphragm 110 may be made of silica, silicon, silicon oxide, or silicon nitride, with a thickness of less than about three microns, or, more preferably, about one micron or less, e.g., about 100 nm or about 750 nm. The diaphragm can be formed of a layer of silica, silicon nitride, silicon oxide, or silicon deposited onto a silicon wafer, which can be removed by etching. This thin film can be made by oxidation of silicon wafers or by low pressure chemical vapor deposition. The silicon wafer can be removed from the thin film layer by either wet etching and dry etching, such as deep reactive ion etching, although dry etching is preferred.

The diaphragm 110 has the thickness and surface characteristics of the thin film deposited on the substrate. For example, silica thin films may have a thickness of anywhere within the range of about 0.1 µm to about 10 µm; more preferably, the thickness is about 1.0 µm or less. The thickness of the diaphragm made from such as thin film is within the range of about 1% to about 10% of the total thickness (or, more preferably, by up to and including 5%), e.g., a diaphragm that is nominally 1.0 µm thick may have an actual thickness of 1.0 µM±0.1 µm. Such a diaphragm is almost perfectly flat at a width of about 20 µm, it has a wedge angle of about 0.15 µrad. In addition, it is very smooth, with a root-mean-square roughness of about 0.2 nm over an area of about 20 µm×20 µm. For more on the characteristics of thin films prepared using deep reactive ion etching, see, e.g., S. Chandrasekaran and S. Sundararajan, "Effect of microfabrication processes on surface roughness parameters of silicon surfaces," Surfaces & Coatings Technology 188-189: 581-587 (2004), incorporated herein by reference in its entirety.

FIG. 1B shows alternative sensor 120 made of an optical fiber 122 with a core 126 and a cladding 124. In this case, however, the sensor 120 includes a cavity 128 between the fiber 122 and a diaphragm 130 with a recess. As above, the diaphragm 130 is formed of a thin film and has a uniform thickness, e.g., a thickness that varies by up to and including about 10%, or, more preferably, about 5%. The diaphragm 130 is preferably made of silica, and can include silicon, silicon nitride or a composite material which has silicon, oxygen, nitrogen or hydrogen. The diaphragm 130 does not need to be precisely aligned to the cladding 124 so long as the end face of the core 126 is aligned to the recess in the diaphragm 130. In general, the end face of the optical fiber 122, including the end face of the core 124, should be aligned parallel to the surface of the diaphragm 130 on the interior of the cavity 128.

FIG. 1C shows another alternative sensor 140 of the invention, made of optical fiber 142 and a silica diaphragm 150. Here, recesses in both the fiber 142 and the diaphragm 150 form parts of a cavity 148. The diaphragm 150 contacts the fiber cladding 144 such that the core 146 opposes the interior surface of the diaphragm 150.

Alternatively, in another embodiment, not shown, a cavity can be defined by a short, fused capillary tube (not shown).

Operation of Optical Fiber Sensors

Figure 2A:
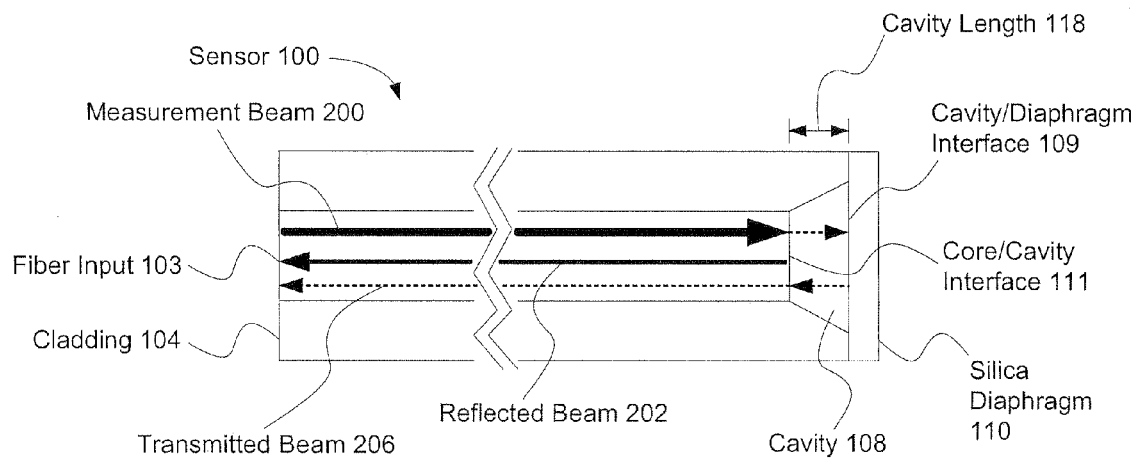
FIGS. 2A and 2B are schematic illustrations of a fiber sensor in operation.
Figure 2B:
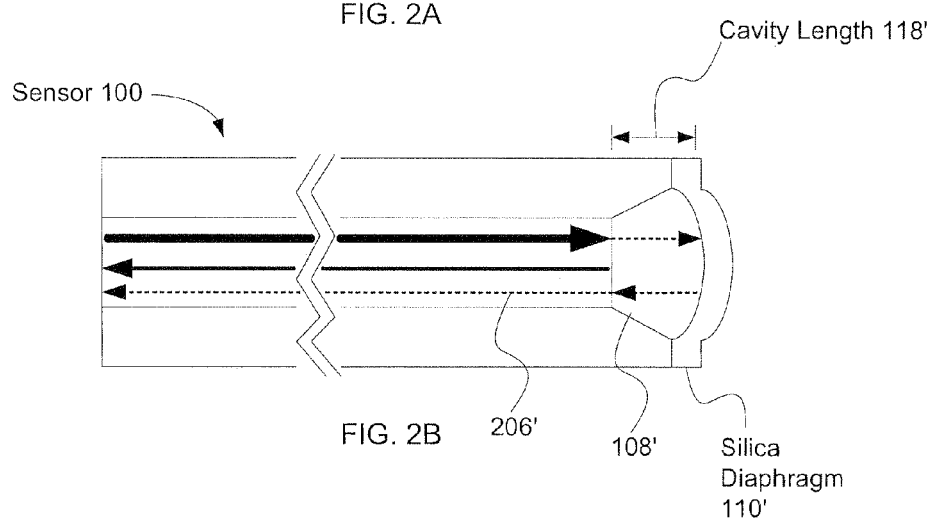

FIGS. 2A and 2B are schematic illustrations of how the fiber sensor 100 of FIG. 1A is employed to detect changes in temperature or pressure. (Sensors 120 and 140 operate in the same manner.) The fiber 102 transmits a measurement beam 200 from a fiber input 103 to a core/cavity interface 111 between the core 106 and the cavity 108. The core/cavity interface 111 reflects part of the measurement beam 200 and transmits the rest. The reflected part, or reflected beam 202, propagates back down the optical fiber 102 towards the fiber input 103.

The transmitted part of the measurement beam, or transmitted beam 206, propagates through the cavity 108 to an interface 109 between the cavity 108 and the silica diaphragm 110. The transmitted beam 206 reflects off the cavity/diaphragm interface 109 and propagates back through the cavity 108. The core/cavity interface 111 transmits (at least part of) the transmitted beam 200, which propagates back down the optical fiber 102 towards the fiber input 103. (Further reflections can occur at each interface in the sensor 100, resulting in spurious signals that can be filtered from the desired signal.)

As the transmitted beam 206 propagates back and forth through the cavity, it accumulates a round-trip phase delay equal to twice the product of the cavity length 118 and the cavity's index of refraction. The accumulated phase delay causes the transmitted beam 206 to interfere with the reflected beam 202 to produce a signal that depends on the phase difference. Changes in the cavity length 118 due to external pressure or temperature changes produce corresponding changes in the measured signal.

As shown in FIG. 2B, for example, when the ambient pressure decreases, the diaphragm 108' bows outwardly, as shown, causing the cavity length 118' to increase, which, in turn, causes the reflected beam 206' to accumulate a greater phase delay. Likewise, increases in ambient pressure cause the cavity length 118 to decrease and the reflected beam to accumulate less phase delay. Changes in temperature may also cause the cavity to expand or contract, resulting in corresponding changes in the detected interference signal.

Figure 2C:
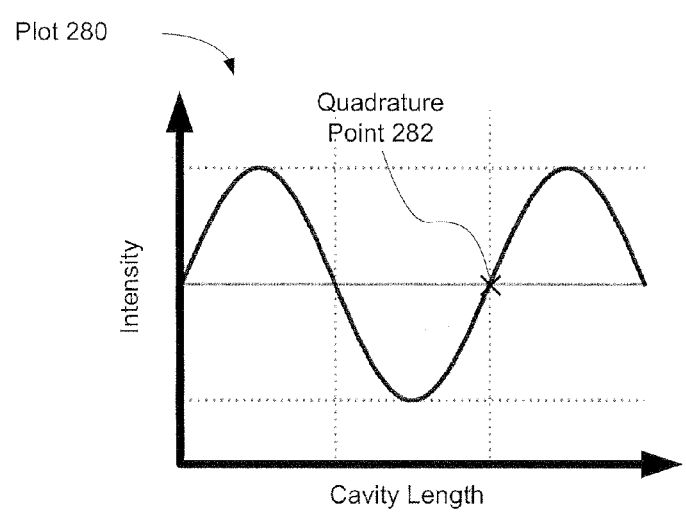
FIG. 2C is a plot of output intensity from the fiber sensor as a function of fiber sensor cavity length.

FIG. 2C shows a plot 280 of the intensity detected at the fiber input 103 as a function of the cavity length 118. The intensity varies sinusoidally with the cavity length according to the equation:

$$I = I_0 + I_m \cos(4\pi n l/\lambda),$$

where n is cavity's index of refraction, l is the cavity length, $\lambda$ is the wavelength of the measurement beam 200, and $I_0$ and $I_m$ depend on the coefficients of reflection of the interfaces 109 and 111. At certain initial cavity lengths, the intensity varies linearly about a quadrature point 282 as a function of cavity length. Setting the initial cavity length to about $(m+\frac{1}{2})(\lambda/4)$, where m is an integer equal to zero or greater than zero, corresponds to fixing the cavity's relaxed length to a quadrature point. The Q point is the center of the linear zone of the spectrum. Although linear variation about the quadrature point is useful for intensity demodulation, the cavity length can vary from $(m+\frac{1}{2})(\lambda/4)$, though the length should preferably remain within the linear range.

Other demodulation techniques can be used to measure pressure or temperature changes. For example, with spectrum demodulation, the entire reflection spectrum is used to determine the pressure by measuring the shift in the spectrum position. With this method, the cavity length is no limitation provided that the length is long enough to have at least one peak or valley within the spectrum measurement range.

The thickness of the diaphragm 110 and the diameter of the diaphragm 110 affect the sensitivity of the sensor. Generally speaking, thinner diaphragms tend to be more sensitive to pressure variations, hence the desire to make diaphragms with thickness of one micron or less.

Making Optical Fiber Sensors

Figure 3A:
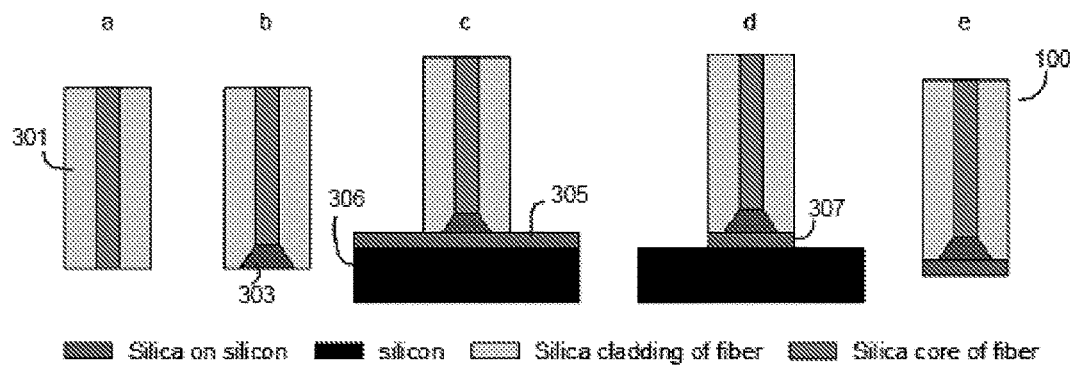
FIGS. 3A and 3B are schematic illustrations of methods of constructing fiber sensors according to embodiments of the present invention.

FIG. 3A shows a method of making an optical fiber sensor 100 according to one embodiment of the present invention. Standard optical fiber 301, shown in (a), is etched in (b) to form a hole or recess 303. In (c), the etched fiber is bonded to silica thin film 305 on a holding substrate 306. Next, in (d), unnecessary silica thin film is removed to form a silica diaphragm 307, which is bonded to the fiber before the holding substrate is removed to release the diaphragm (e). The fiber can also be bonded to the silica after the excess silica is removed.

The thickness of the diaphragm depends on how thick the silica can be grown on the silicon wafer, and can be under about 3 μm thick, under about 1 μm, and even as thin as 100 nm. Commercially available silicon wafers may be used to lower costs and to make handling easier; typical commercially available wafers have silica layers that are within a range of about 50 nm to about 10 μm thick. The diaphragm can also be made thinner by etching it after it has been bonded on the fiber.

Figure 3B:
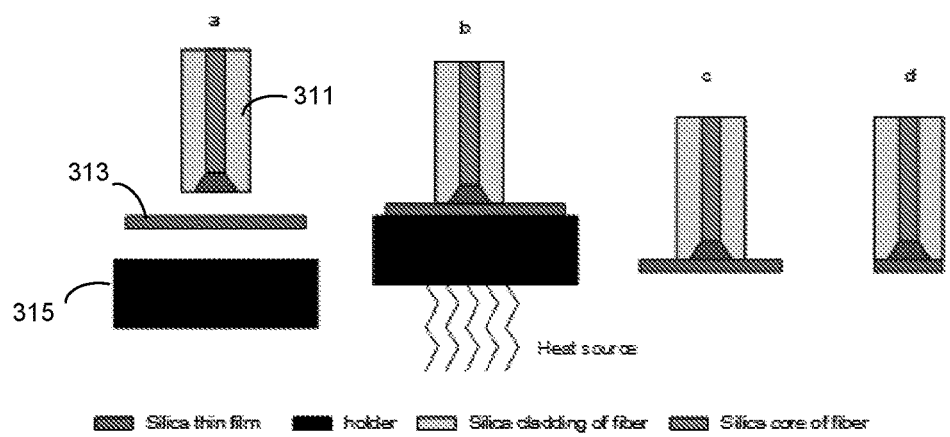

FIG. 3B shows an alternative method of making an optical fiber sensor by bonding thin silica (silicon dioxide) film 313 directly onto the end face of an optical fiber 311 with a recess. A silica-on-silicon wafer is etched with silicon wet etching, such as potassium hydroxide (KOH) wet etching, or dry etching, such as silicon deep reactive ion etching, to remove the silicon substrate from the silica thin film 313. Etching is a selective process; that is, it involves removal of the silicon, but not the silica 313. After the silicon is etched away, only the silica film 313 is left. The wafer can be patterned before etching to keep some silicon as a frame to hold the thin oxide layer (not shown). Etching can also be performed after the thermal bonding described below.

As shown in (a), the film 313 is placed between a fiber with a recess 311 and a holder 315, which should be able to survive in high temperature without sticking to the oxide. Next, the silica layer 313 is thermally bonded (b) to the optical fiber 311. Alternatively, the recess formed in (b) of FIG. 3A can be formed by hydrofluoric (HF) etching and, optionally, splicing, the end face of a single-mode optical fiber. Because the core and cladding of the fiber 311 have different doping levels, their etching rates in HF solution are different. Proper etching produces a recess in the core without excessive removal of the cladding.

After thermal bonding, a ferrule (not shown) is placed around the fiber 311. The ferrule's inner diameter should match the fiber's outer diameter to ensure a snug fit. Once the ferrule is in place, the holder is removed (c) and the silica film 313 beyond the area of end face of the optical fiber 311 is cut away (d). If the holder is a silicon substrate, it can be etched away with an alkaline-based solution, such as KOH in water. Because the etching rate for silica is much lower than the etching rate for silicon, the silica thin film acts a natural stop layer for silicon wet etching. This makes the release process simple: once the optical fiber is bonded to silica thin film on a silicon substrate, the assembly can be dipped into an alkaline solution until all the silicon is removed. When oxide thin film without a substrate is used, there is no need to etch away silicon.

Some sensors may need cavities whose diameters exceed the diameter of a single-mode fiber core. These cavities can be formed by splicing a piece of multimode optical fiber to the single-mode optical fiber, then cleaving the multimode fiber to the desired length before etching away the multimode core to form a recess as in (b) of FIG. 3A.

Silica thin film can be fabricated using any one of several approaches. Thermal oxidization is cost efficient when using silicon wafers, which are available with thermal oxide layers that range in thickness from 0.05 μm to 10 μm. Other deposition methods, including plasma-enhanced chemical vapor deposition (CVD), low-pressure CVD, and sputtering, can be used to deposit silicon oxide with modified physical and mechanical properties onto silicon wafers. For example, the ratio of silicon to oxygen or the coefficient of thermal expansion (CTE), which is related to the amount of stress exerted on the thin film, can be varied by adjusting the process parameters. Changing the properties of the silica thin film makes it possible to alter or improve the performance of sensors constructed with the silica thin film. A straightforward improvement is to use a silicon oxide thin film whose CTE matches that of the optical fiber, thereby eliminating thermal drift in the sensor caused by materials with mismatched CTE.

Figure 4:
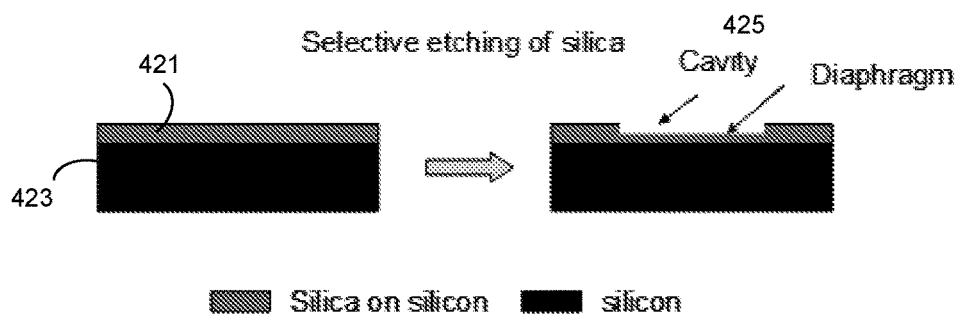
FIG. 4 is a schematic illustration of a method of etching a recess in a silica thin film according to embodiments of the present invention.

FIG. 4 shows a method of making a sensor by etching a recess in the diaphragm instead of the optical fiber. For example, the recess can be etched into a 5 μm silica thin film 421 on a silicon substrate 423. Selectively removing part of the top oxide layer yields a shallow hole 425, as shown in FIG. 4, which can be sealed with an optical fiber to form a cavity. Recesses can also be fabricated in both the end face of optical fiber and the silica layer at the same time, and the resulting pieces can be bonded together to form the cavity. Those skilled in the art will understand that other cavity forming methods can be used without significant differences in performance.

Bonding Silica to Optical Fiber

Thermal fusion bonding is a good way to bond silica thin film to an optical fiber end face. However, high temperatures cause the thin film to deform greatly when heated to or above its softening or melting points. High temperatures also cause the optical fiber to deform and changes the refractive index distribution within the core and cladding of the optical fiber. To obtain high-quality bonding between the thin film and optical fiber tip, a substrate holder should be used to hold the silica film and the heating zone should be confined to the vicinity of the optical fiber tip and the thin film. Localized heating allows the interface to reach high temperature more quickly, minimizing deformation and index changes. Another advantage is that thermal fusion bonding does not require parts to have extremely flat, smooth bonding surfaces, as needed for lower temperature processes. Eliminating the need for flat, smooth surfaces significantly lowers the cost of the final product. During thermal bonding, the optical fiber and/or the diaphragm are heated, e.g, to about 200° C. or above for silica diaphragms or to about 700° C. and above for silicon diaphragms. (Polishing the fiber before heating may reduce the temperature required to bond the fiber to the diaphragm.) After cooling down, mechanical stress may exist between the substrate and the diaphragm due to the differences in their CTE. Removing the substrate should release this stress, which can make the structure very fragile. Choosing a sufficiently thin substrate also reduces the mechanical stress. On the other hand, reducing the substrate thickness reduces support force for the thin silica film during fusion bonding. The silicon-silica two-layer structure can also deform, causing the film/substrate to push against the fiber. Therefore, the silicon substrate thickness should be selected carefully according to the thickness of the silica thin film and the bonding parameters.

During bonding, the reflection spectrum can be monitored in real time to give an indication of the cavity length. The cavity length can be precisely adjusted by adjusting the heating power, heating time, and force applied to push the fiber and thin film together. Because the diaphragm is fixed on the silicon substrate, adjusting the cavity length does not affect the quality and shape of the diaphragm.

Silicon and silica have different absorption coefficients for wavelengths between six and fourteen micron. In that range, silicon is partly transparent while silica strongly absorbs. In the wavelength range between 350 nm and 1.1 μm, the behavior of silicon and silica reverses: silicon absorbs strongly, whereas silica is transparent. Thus, either the silicon or the silica can be heated selectively with a readily available high-power laser at an appropriate wavelength.

Figure 5A:
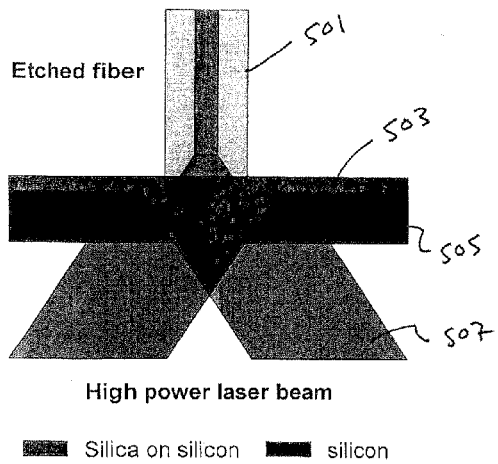
FIGS. 5A-5F are schematic illustrations of methods of localized heating of silica diaphragms and optical fiber tip according to embodiments of the present invention.

FIG. 5A illustrates selectively heating a silica/fiber interface with a 10.6 μm $CO_2$ laser. Collimated laser beams 507 pass through a silicon substrate 505 before being absorbed at the interface of a silica thin film 503 and an optical fiber 501. As shown in FIG. 5A, a sufficiently large, collimated beam 507 can be used to heat the whole surface of the fiber end face, eliminating any complex laser focusing and scanning requirements. Because the laser beam 507 is collimated, it has a long working distance, which makes it easier to design and use the bonding system.

Figure 5B:
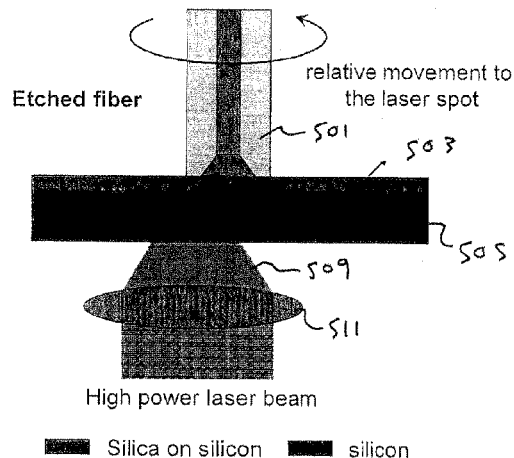

FIG. 5B shows an alternative laser fusion bonding involving a focused laser beam 509. Focusing the beam increases the intensity and reduces the illuminated area, making it possible to heat a small spot quickly and precisely, reducing thermally induced stress. (Diffraction limits the minimum spot size.) Mounting the laser (not shown), a focusing lens 511, or substrate/fiber to a stage or steering the beam with a mirror or other deflector makes it possible to move the focused spot relative to the fiber/silica interface. A fiber 501 and thin film 503 can be bonded by the moving beam 509 or the substrate/fiber 503/501 along a designed path at a given speed or sequence.

Figure 5C:
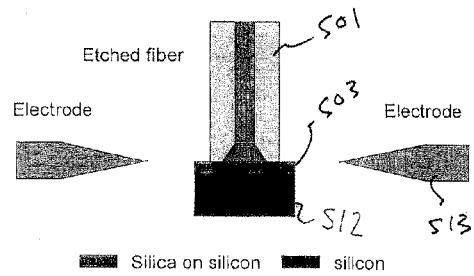

FIG. 5C shows thermal fusion bonding of an optical fiber 501 and a silica thin film 503 via electrical discharge, or splice bonding. Although splice bonding is well-known for bonding optical fibers, it has not yet been used to bond etched optical fiber 501 and silica-on-silicon dies 512, possibly because of difficulties in securing the dies 512 and fibers 501 between electrodes 513.

First, a die 512 is cut from a silica-on-silicon wafer with a dicing saw or using deep RIE. Preferably, the die size is similar to the diameter of the optical fiber, i.e., it is a circle about 125 μm in diameter. Next, a small piece of the die 512 is fixed on a holder, such as a piece of optical fiber, with high temperature cement or any other suitable adhesive. The die 512 and holder are secured between the electrodes 513 of a commercially available fusion splicer, then brought close to the end face of an etched optical fiber 501, as shown in FIG. 5C. Once the fiber 501 is aligned to the die 512, an arc discharged between the electrodes 513 splices the fiber 501 to the die 512.

Figure 5D:
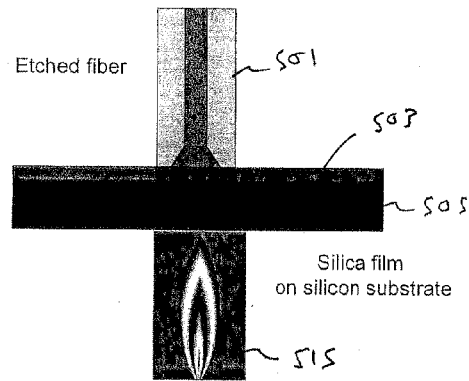

FIG. 5D shows thermal fusion bonding of silica 503 on a silicon substrate 505 to an etched fiber 501 using flame heating. A high-temperature flame 515 heats a silicon substrate 505. The silicon substrate 505, which is a good thermal conductor, conducts heat to the silica thin film 503, which is a good thermal insulator. Heat conducted by the silicon 505 to the silica 503 causes the silica 503 to heat up until the interface between the silica 503 and the fiber 501 reach the desired temperature, which is typically at least about 700° C. (and can be 800° C. or even 1000° C.), the temperature at which silica begins to soften. Other materials, such as silicon nitride, can be heated to higher temperatures to ensure proper bonding.

Figure 5E:
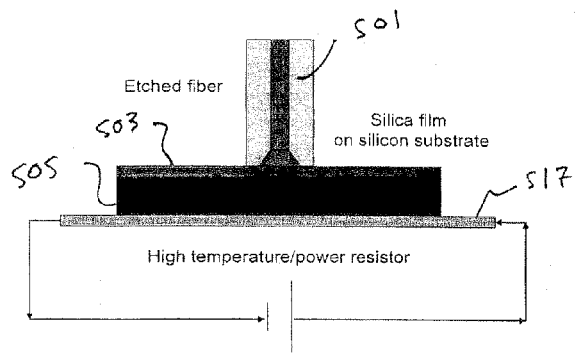

FIG. 5E shows thermal fusion bonding of silica 503 on a silicon substrate 505 to an etched fiber 501 using electrical resistor heating. The substrate 505 is placed on a resistor 517, which, like a filament lamp, can be heated to over 700° C. almost instantaneously with a large enough current. Because silicon has very good thermal conductivity and silica does not, only the silica thin film 503 and the optical fiber tip 501 reach the desired temperature of at least about 1000° C. Electrical resistor heating can be done in a vacuum environment.

Laser fusion bonding and electrical resistor heating can be conducted under vacuum to produce a sealed cavity with better reference pressure. When gas is sealed in the cavity between the fiber and the diaphragm, the pressure in the cavity varies with temperature. The cavity can deform due to differences between the internal and external pressures. A vacuum cavity suppresses this response, giving the sensor a better reference pressure and better stability in environments with large temperature variations.

Figure 5F:
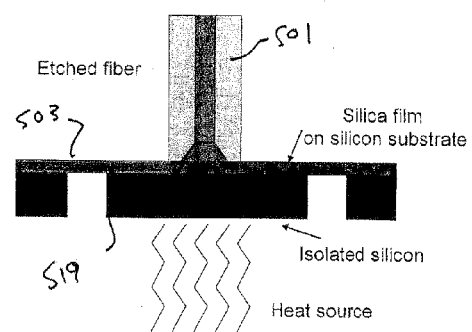

FIG. 5F shows alternative thermal bonding using an isolated silicon substrate 519. To reduce heating time and save energy, the silicon substrate under the fiber tip can be isolated from the rest of the substrate by selectively removing portions of the substrate. The silica thin film 503 transfers very little, if any, heat because its conductivity is low and its transfer cross-section is small.

Figure 6:
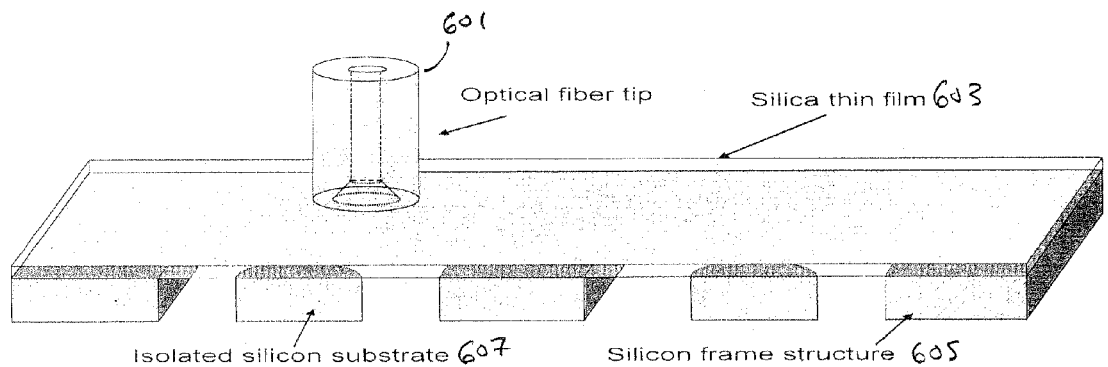
FIG. 6 is a schematic illustration of an optical fiber in contact with a silica thin film on a silicon frame structure.

FIG. 6. shows an etched optical fiber 601 in contact with a silica thin film 603 on a silicon frame structure 605. An isolated silicon substrate (island) 607 supports the silica thin film 603 under the fiber 601. The frame structure 605 and substrates 607 can be made by selectively etching a silicon wafer using MEMS technology. Once the frame structure 605 and substrates 607 are etched into the wafer, the optical fibers 601 can be bonded to the thin film 603 on the wafer above each silicon island 607 by heating to at least about 1000° C., as described above. Because the silicon islands 607 are isolated from each other, they do not influence each other (e.g., by conducting heat).

Figure 7A:
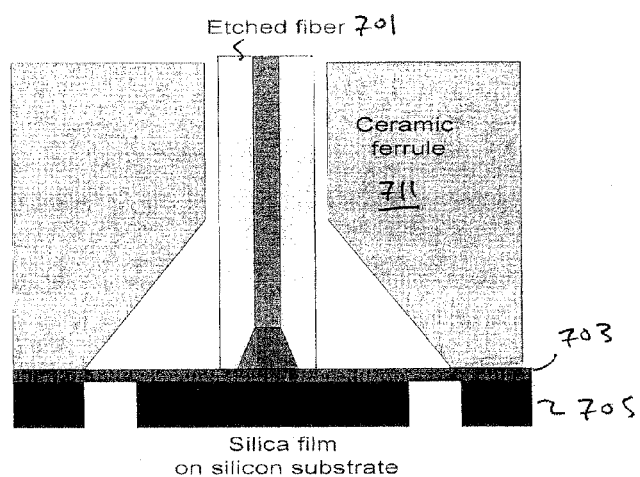
FIG. 7A is a schematic illustration of an etched optical fiber in a ferrule in contact with a silica thin film on a silicon frame structure.

FIG. 7A shows an optical fiber 701 held in position with a ceramic ferrule 711 above a silica thin film 703 on a silicon frame structure 705. Standard optical fiber ferrules, such as the ceramic ferrule 711, can be used to handle the optical fiber 701 during fabrication of optical fiber sensors. The ferrule 711 has an inner diameter that is just a little larger than the outside diameter of the optical fiber 701 and an outer diameter of a few millimeters. The ferrule's end face is flat. The ferrule 711 includes a cone-shaped holder on one side and is an ideal structure for holding the optical fiber during thermal bonding. Optionally, the flat side is also good to use when it is desired to hold as much of the fiber tip or to hold the tip from another angle. For example, when the cavity length is to be adjusted, the fiber is pushed, but done so as to not cause the fiber to curve, so the flat end is used.

Figure 7B:
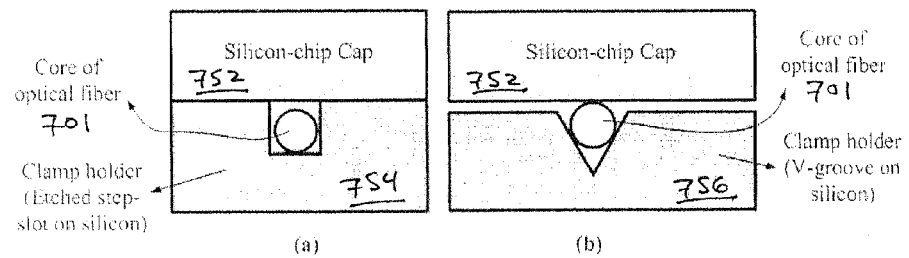
FIG. 7B is a schematic illustration of optical fibers held in place by silicon chips with either step-slots or V-grooves.

FIG. 7B illustrates two alternative ways of securing an optical fiber 701 during fabrication of an optical fiber sensor. These alternatives involve holding the fiber 701 in place is using a silicon cap 752 and one of two silicon chips 754 and 756 instead of a ceramic ferrule. The chip 754 shown at left (a) has a step-slot fabricated by HF wet etching, whereas the chip 756 at right (b) has a V-groove. Chips with V-grooves are readily available in the market. The fiber 701 is placed in either the step-slot or the V-groove and a silicon cap 752 is pressed on to hold the fiber 701 in place. Compared with the step-slot structure 754, the V-groove structure 756 can hold the fiber 701 tighter but may be less flexible. These two clamp holders 754, 756 can be selected depending on the bonding force needed and fragility of the fiber.

Wireless Communication with Optical Fiber Sensors

Figure 8:
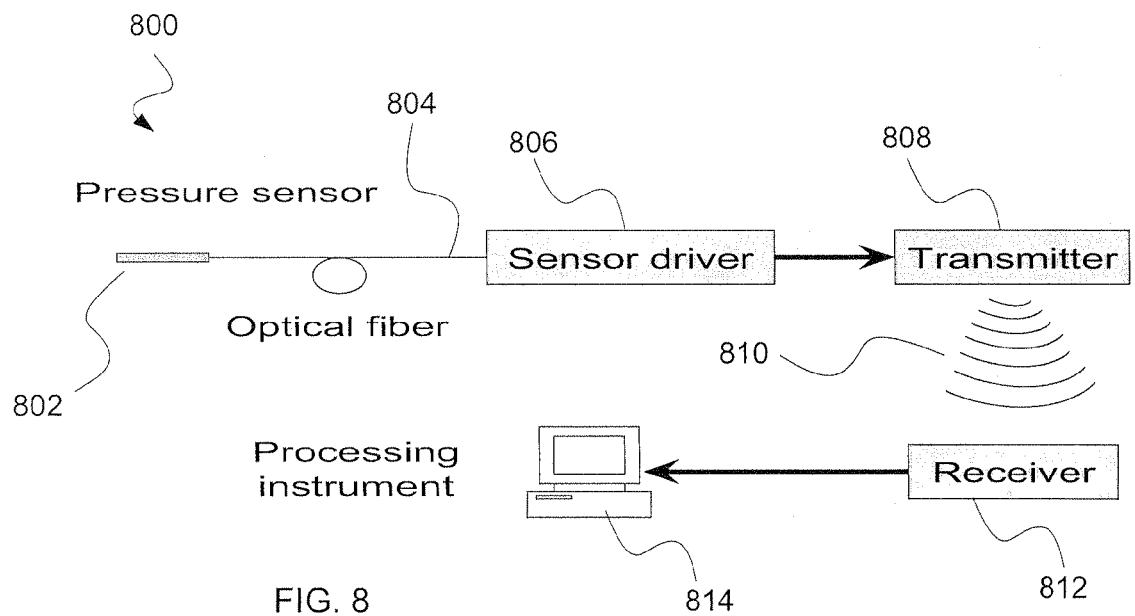
FIG. 8 is a schematic illustration of a wireless communication system suitable for use with optical fiber sensors.

FIG. 8 is a schematic diagram of a wireless communication system 800 suitable for use with an optical fiber sensor 802. Wireless communication enables real-time blood pressure measurement and monitoring while isolating the patient from contamination from system 800. Radio technology provides instant wireless access, as in the PressureWire® Aeris, built by Radi Medical Systems' in cooperation with General Electric Healthcare. Despite its maturity, however, radio technology can cause undesirable electromagnetic interference (EMI). Therefore, infrared (IR) wireless communication is used here because it does not introduce EMI.

As shown in FIG. 8, the wireless communication system 800 includes a transmitter 808 and a receiver 812. The transmitter 808 receives an output signal from an optical fiber sensor 802, which is connected to the transmitter 808 via an optical fiber 804 and a sensor driver 806. The transmitter 808 encodes the output signal according to standard protocols, then transmits a corresponding IR signal 810. The receiver 812 receives an IR signal 810 and sends it to a computer 814 for processing. The sensor driver 806 and transmitter 808 can be placed on the operating table and the receiver 812 can be placed elsewhere, depending on the wireless protocol and the layout of the operating room.

Standards now available now for IR wireless communication include the Infrared Data Association Standards (IrDA), for point-to-point communication with an operating range from 0-1 m, and the IEEE 802.11 and wireless LANs standards, for links up to 10 m long. These standards can be used for surgical applications.

Pressure Measurements with Example Fiber Sensors

Figure 9A:
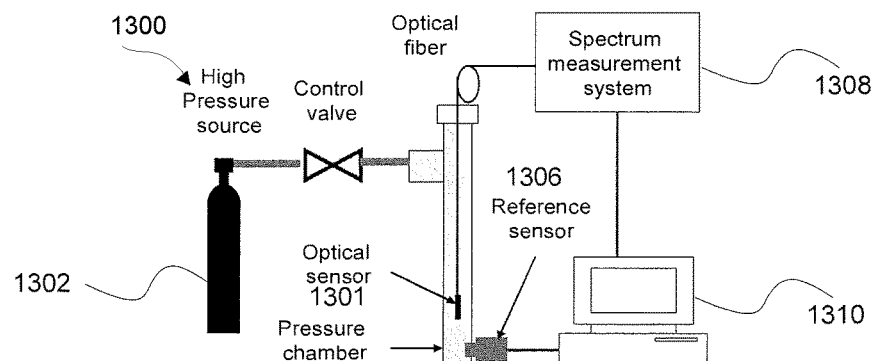
FIGS. 9A-9C are illustrations of the fiber sensor characterization setups.
Figure 9B:
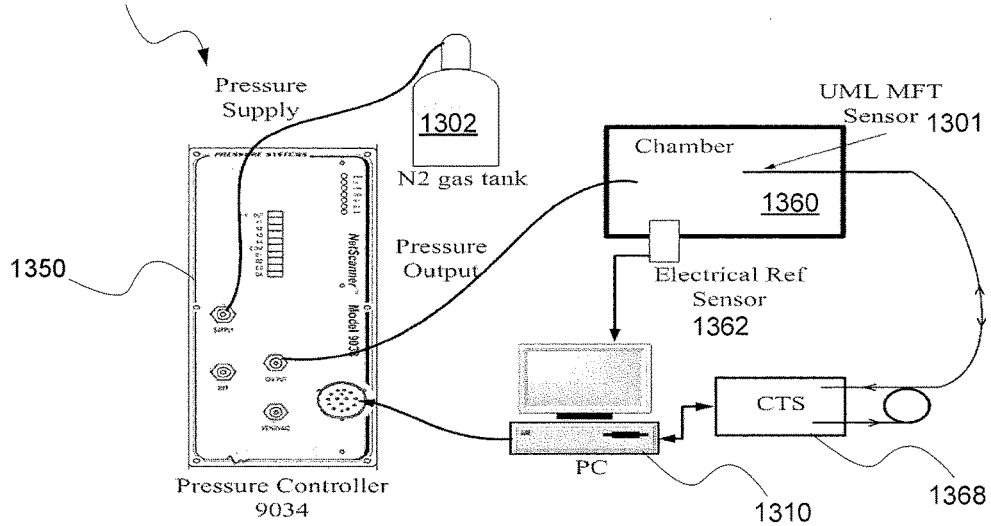
Figure 9C:
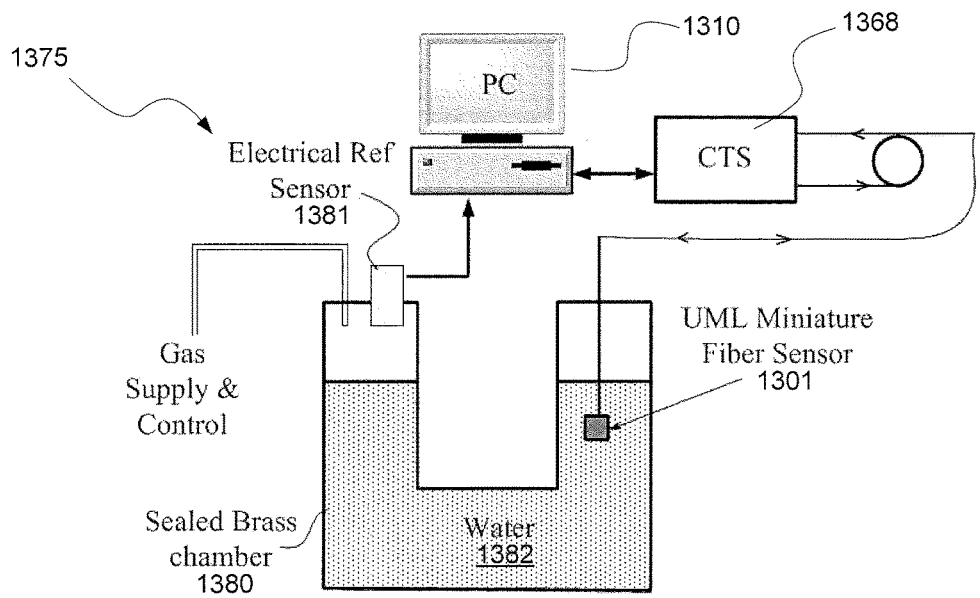

FIGS. 9A-9C are illustrations of various pressure measurement systems for testing fiber sensors 1301. FIG. 9A shows a pressure measurement system 1300 (employing an Omega PX303 pressure sensor) for testing a fiber sensor 1301. A pressure source 1302 applies pressure via a control valve 120 to the sensor 1301, which is in a pressure chamber 1304. A spectrum measurement system 1308 senses changes in the reflection spectrum of the sensor 1301. A data acquisition system 1310 records the changes measured by the spectrum measurement system 1308 and pressure changes measured by a reference sensor 1306 to characterize the precision of the sensor 1301.

FIG. 9B shows an alternative pressure measurement system 1330 that features automated control of the pressure applied to a sensor 1301 in a nitrogen-filled test chamber 1360. A reference sensor 1362 coupled to the chamber senses the chamber pressure and feeds pressure information to a computer 1308, which is coupled a pressure controller 1350 (Model 9034, Pressure Systems Inc.) that controls the pressure in the test chamber. The computer 1308 also records measurement data obtained with the sensor 1301 and a component testing system (CTS) 1368 for later analysis.

FIG. 9C is a diagram of a setup 1375 for measuring the performance of a fiber optic sensor 1301 in water 1382. An electropneumatic transducer (IP-413, Omega) is connected to a chamber 1380 filled with water 1382. The electropneumatic transducer acts as a valve that controls the pressure in the chamber. During testing, the optical fiber sensor 1301 and a reference sensor 1381 (PX303-030G5V, Omega) are installed in the chamber 1380. The fiber sensor 1301 is then immersed in water 1382 and the reference sensor 1381 detects the pressure in air. A component testing system 1368 gets signals from the fiber sensor 1301. A computer 1308 obtains, compares, and stores the signals from the fiber sensor 1301 and electrical reference sensor 1381.

EXEMPLIFICATION

The following examples illustrate optical fiber sensors and methods of making optical fiber sensors without limitation of the claims.

Example 1

Fabrication of an Optical Fiber Sensor

Figure 10:
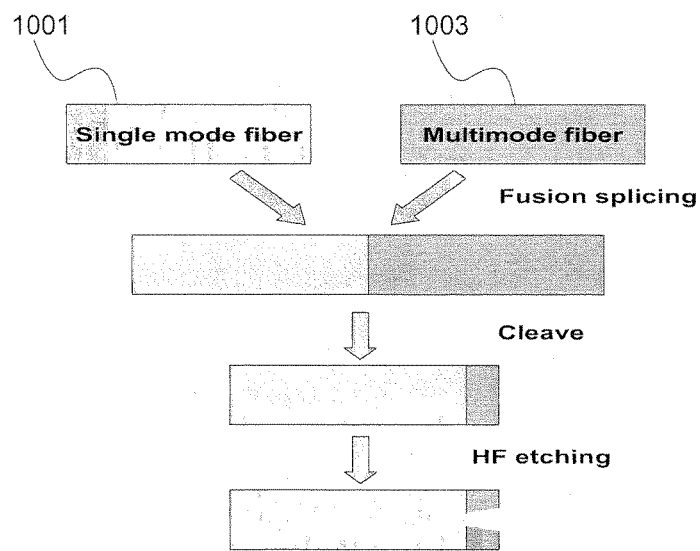
FIG. 10 is a schematic illustration of making an etched fiber from single-mode and multimode fiber.

FIG. 10 shows how the recess was etched into the fiber tip. Single-mode fiber 1001 (SMF-28, Corning) was fusion-spliced to graded-index multimode fiber 1003 with a 62.5 µm diameter core. Next, the fiber was cleaved at multimode fiber 1003 near the connection point between the single-mode and multimode fibers. The length of the multimode fiber ranges from 20-100 µm in order to have one or more valleys in the reflection spectrum from 1520 nm to 1570 nm (the wavelength range of the spectrometer) to ensure that spectral shifts could be measured accurately.

Then, the fiber was etched using 49% HF for 330 seconds. Because the core of multimode fiber 1003 has much higher etching rate than other parts of fiber 1003, etching exposes a recess in the fiber end face. As noted above, the recess can be etched directly into single-mode fiber 1001, but recesses etched into single-mode fiber 1001 tend to be narrower and shallower than recesses etched into multimode fiber 1003.

Next, a double-sided, polished silicon wafer with a thermal oxide layer was used to fabricate the silica thin film. Silicon wafers with 1 µm and 3 µm silica films were used for demonstration. One side of the oxide was partly removed by reactive ion etching (RIE). Then the silicon was etched away with KOH solution or RIE to leave only the thin film.

The sensor was then assembled according to the process shown in FIG. 3B. First, a thin film was placed between the tip of the optical fiber, which is held in a zirconia ferrule with a 128 µm diameter hole (Kientec, Inc.). The fiber tip, thin film, and ferrule were heated with a propane torch while the thin film was pressed against the fiber. Once the fiber was bonded to the thin film, the thin film beyond the end face of the optical fiber was removed by pulling the fiber through the ferrule.

Figure 11A:
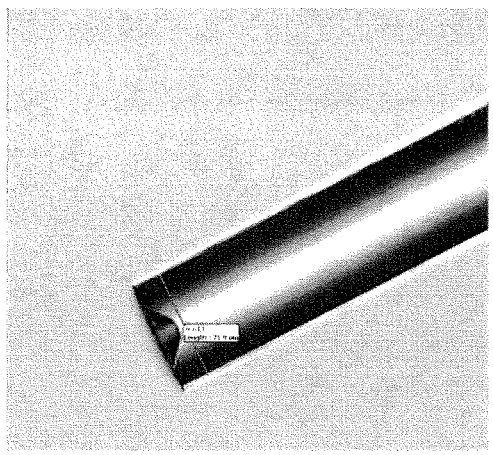
FIGS. 11A and 11B are photographs of an etched fiber and an optical sensor, respectively, according to embodiments of the present invention.
Figure 11B:
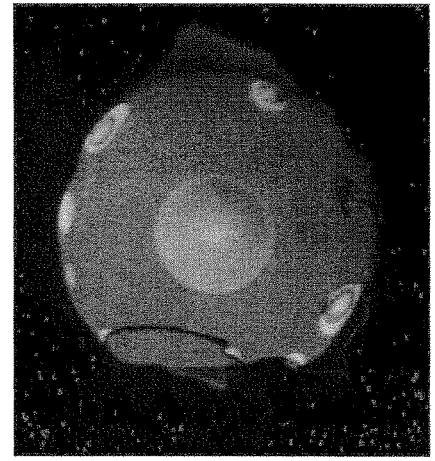

FIGS. 11A and 11B are photographs of an optical fiber sensor. A standard zirconia ferrule was used to support the thin film and the optical fiber during fabrication. FIG. 11A shows the optical fiber with a recess etched using HF. FIG. 11B shows the end face of the fiber sensor after the oxide thin film was bonded to the end face of optical fiber. Light shading in the center indicates that the thin film is suspended over the cavity and the darker shading indicates the bonding area. The shaded area near the edge of the fiber tip indicates imperfect bonding caused by an uneven surface or dust.

Figure 12A:
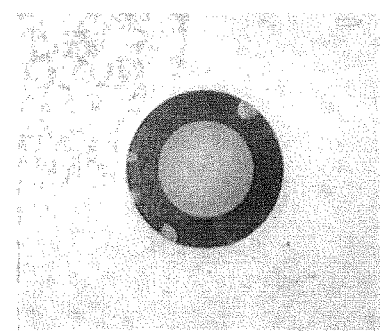
FIGS. 12A and 12B are photographs of end faces of optical sensors according to embodiments of the present invention.
Figure 12B:
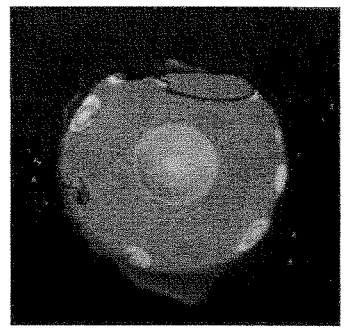

FIGS. 12A and 12B are photographs of thin-film silica bonded to the end of the etched fiber tip. Darker shades indicate that the thin film has been bonded (no reflection). Lighter areas indicate poor or no bonding. Differences in the optical refraction index between the film and the fiber tip produce reflections at index discontinuous positions, including the interior edge of the cavity.

Example 2

Test Data for an Optical Fiber Sensor with a 3 µm Thick Diaphragm

Figure 13A:
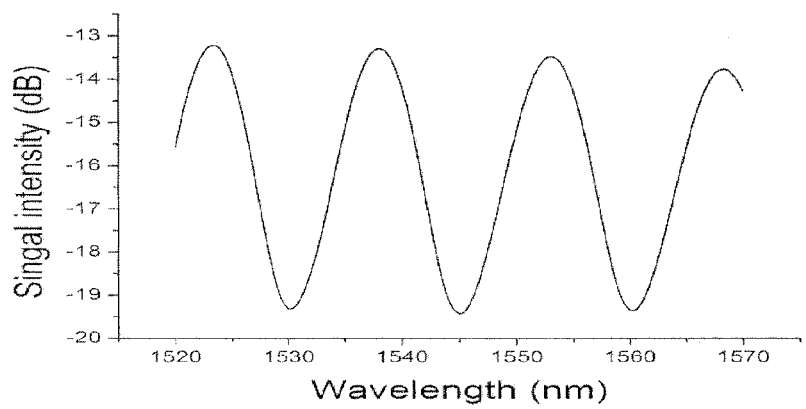
FIGS. 13A-13C are plots of pressure measurements made using an example sensor.
Figure 13B:
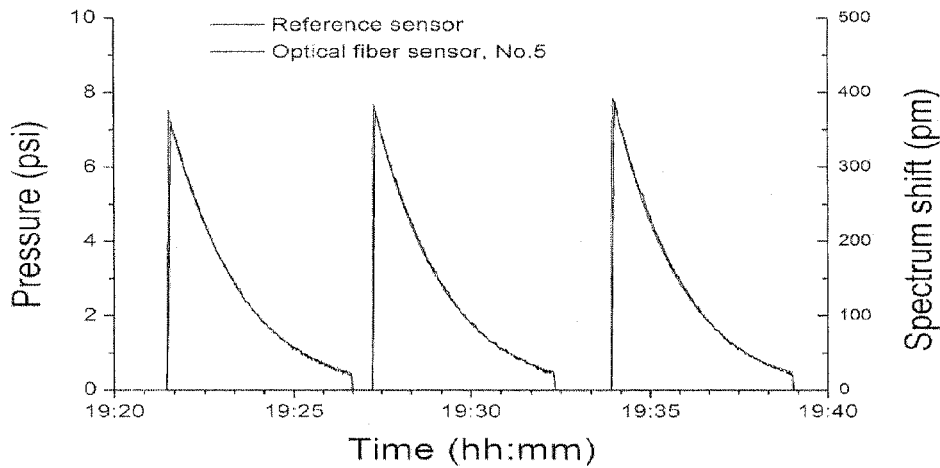
Figure 13C:
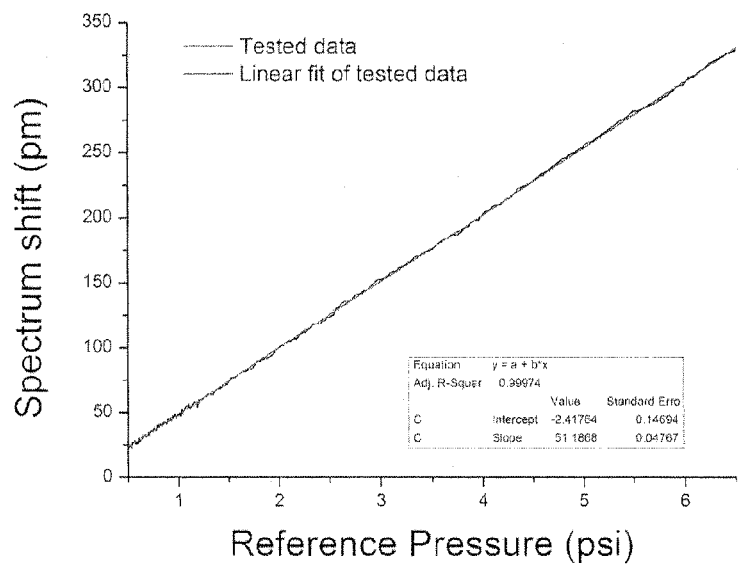

FIG. 13A is a plot of the reflection spectrum from a fiber sensor with a 3 µm thick diaphragm on a multimode fiber with a 62.5 µm core diameter. Based on the period of the reflected fringe, the cavity length is about 70 µm. FIG. 13B is a plot of the spectral shift (in picometers) measured by the fiber sensor and the pressure shift (in pound per square inch) measured by the reference sensor as a function of time. The two plots line up well, indicating the fiber sensor's high precision. FIG. 13C is a close-up of one of the cycles shown in FIG. 13B. FIG. 13C shows that the fiber sensor exhibits good linearity (the correlation coefficient of the test curves and the linear curve is R-0.9974, and compares well to the reference sensor. The sensitivity of the spectral shift is about 51 µm/psi and can be further improved by fabricating diaphragms with thinner or larger diameter.

Example 3

Multi-Cycle Test Data for an Optical Fiber Sensor

Figure 14:
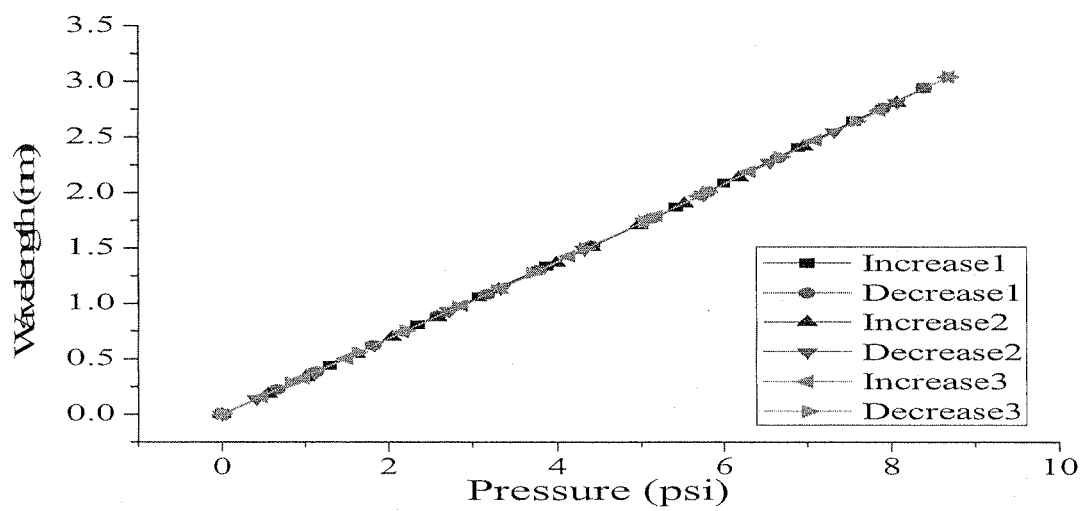
FIG. 14 is a plot of pressure response from the sensor versus notch wavelength shift.
Figure 15:
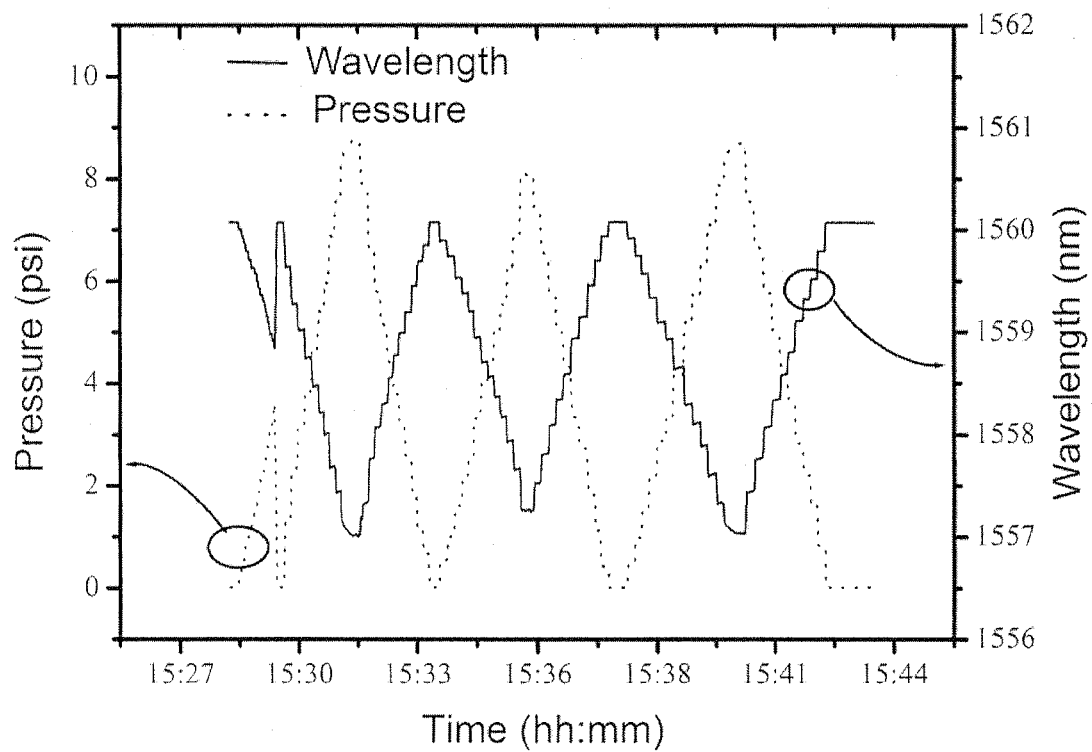
FIG. 15 is a plot of pressure change and wavelength shift versus time for three cycles of pressure fluctuation.

FIGS. 14 and 15 show further test data from example fiber sensors. FIG. 14, like FIG. 13C, is a plot of notch wavelength shift versus pressure for three pressure cycles over a range of 0-9 psi. FIG. 15 shows pressure and wavelength versus time for three pressure measurement cycles over a range of 0-9 psi. The overlap of the points in FIG. 14 shows that the inventive optical fiber sensor exhibits good linearity and very small hysteresis. The slope of the line plotted in FIG. 14 is the sensitivity of the fiber sensor, which, in this case, is about 0.35 nm/psi. The correlation coefficient between pressure change and wavelength shift is 0.99996 which means the sensor has very good linearity. The maximum difference between increasing wavelength shift and decreasing wavelength shift is 0.126% which shows low hysteresis that is, the deviation between measurements of increasing and decreasing pressure over the same range is relatively small, e.g., about 0.3% or less.

Example 4

Optical Fiber Sensor Packaged for Intravascular Applications

One of the important applications of this inventive optical fiber pressure sensor is for measuring blood pressure directly inside blood vessels. Then a flexible and bio-compatible packaging catheter structure is needed for the intravascular use. FIGS. 16A-16E show a fiber sensor apparatus 1200 that uses one of many suitable packaging solutions. A piece of over 6-foot-long optical fiber 1206 with a sensor 1202 at its tip is placed inside a continuous stainless steel coil 1210. The coil 1210 includes a long section that is tightly wound 1214 and a loosely wound section 1212 extending over about 1.0 inch of the coil's distal end. (Here, distal refers to the end of the apparatus 1200 inserted into the blood vessel, and proximal refers to the other end of the apparatus 1200.) The loosely wound section 1212 of the coil 1210 is stretched to open up gaps to provide access for the sensor 1202 to blood in the blood vessel. The loosely wound section 1212 can also make the coil 1210 softer, which makes it easier for the distal end of the fiber sensor apparatus 1200 to move inside the blood vessel.

A heat-shrink polytetrafluoroethylene (PTFE) tube 1230 disposed outside the closed coil section 1214 provides added stability and column strength. A stainless steel bead 1220 is laser-welded at the very distal tip of the open pitched coil section 1212. The fiber sensor 1202 is placed inside the coil 1210 about 0.078 inches proximal to an interface 1216 between the tightly wound section 1214 and loosely wound section 1212 of the coil 1210. This allows the tightly wound section 1214 to protect the sensor 1202 but still provides good access to incoming blood. Stainless steel and PTFE are both biocompatible and widely used in various medical applications, including intravascular applications.

Figure 16A:
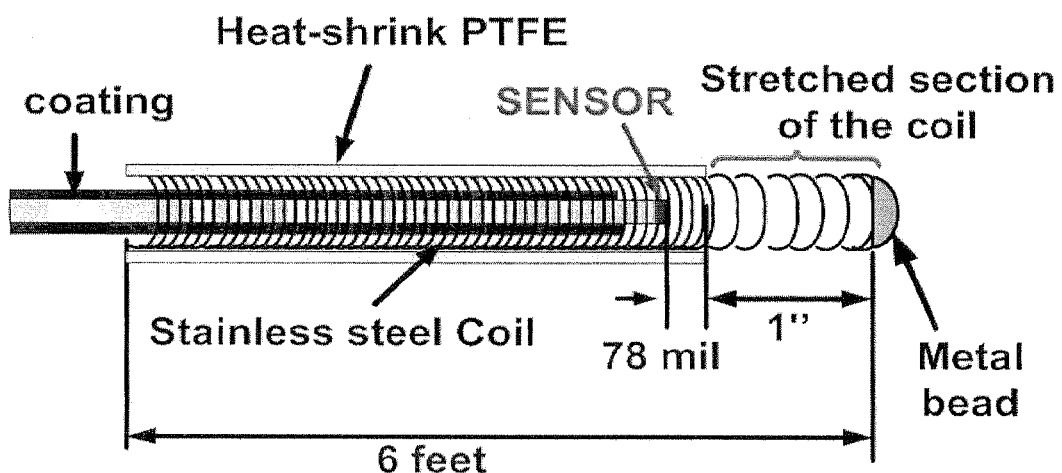
FIGS. 16A-16E are diagrams and photographs of an optical fiber sensor packaged inside a bio-compatible catheter structure.
Figure 16B:
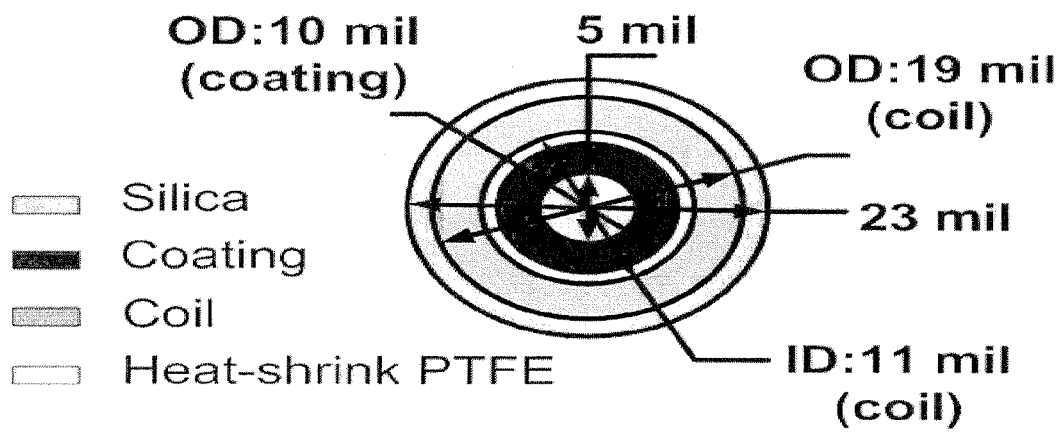

FIG. 16B is a cross-section of fiber sensor apparatus 1200 that shows the diameters of the optical fiber 1206, the stainless steel coil 1210, and the heat-shrink PTFE tube. There is 0.001 inch difference in diameter between the OD of optical fiber coating and ID of coil to insure easy-installation, stabilities and ventilation.

Figure 16C:
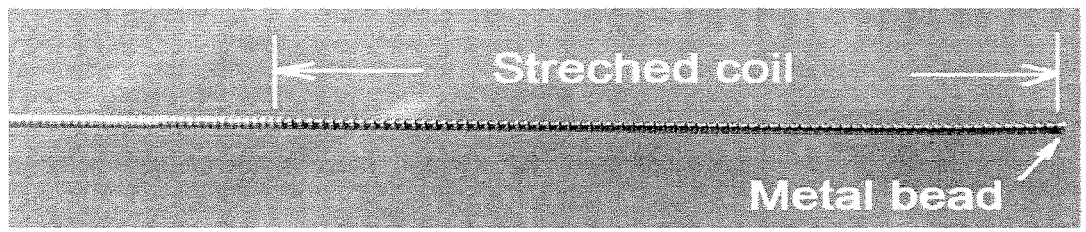
Figure 16D:
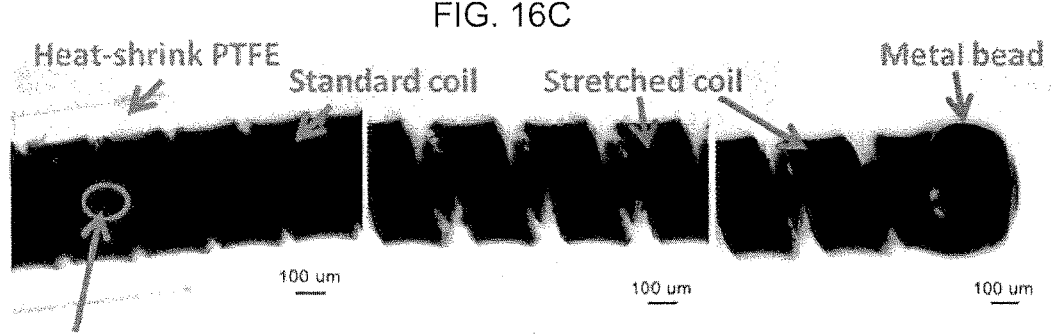
Figure 16E:
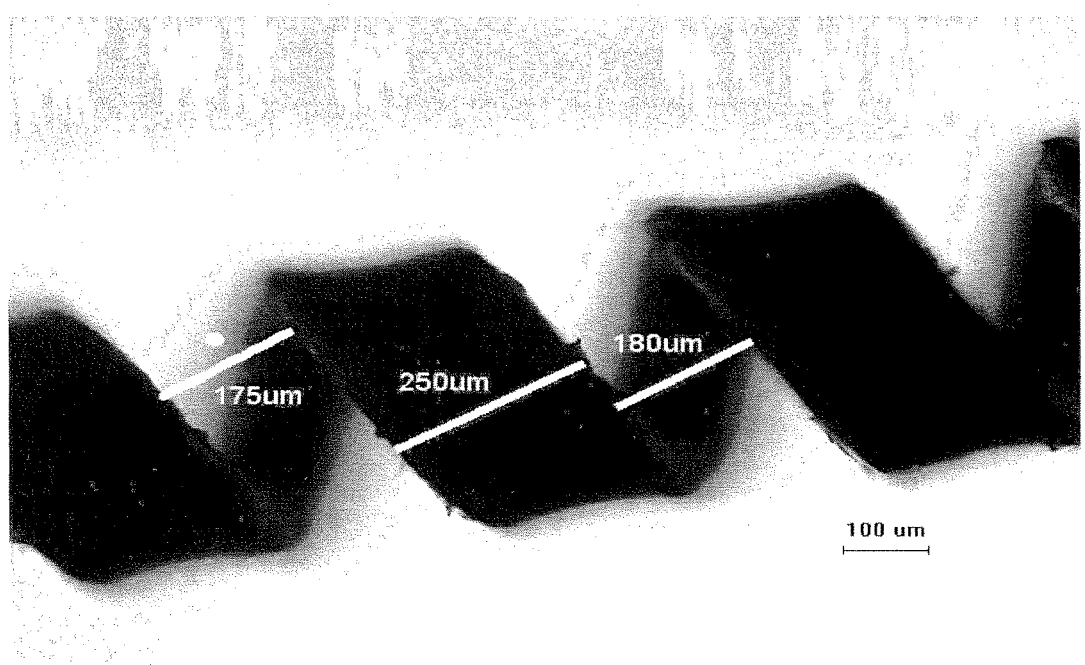

FIGS. 16C-16E are photographs of an example fiber sensor apparatus 1200. FIG. 16C shows the interface 1216 between the tight coil section 1214 and the stretched coil section 1212. FIG. 161) is a close-up of the distal end of the apparatus 1200 that shows the metal bead 1220, stretched coil 1212, tightly wound coil 1214, and heat-shrink PTFE tube 1230 that surrounds the coil 1210. FIG. 16E shows that each coil is about 250 μm thick and that the separation between adjacent coils in the loosely wound section 1212 is about 175-180 μm.

Example 5

Animal Study Demonstration of Intravascular Blood Pressure Sensing

FIG. 17 shows a fiber sensor measurement schema that uses a laser beam instead of electric current to measure intravascular blood pressure. A laser beam generated by a tunable laser (TLB-6600; New Focus) launches through a circulator into an optical fiber sensor introduced into the blood vessel of interest. The optical fiber sensor, which is made using the techniques described above, includes a Fabry-Perot structure on the tip of the optical fiber that reflects two laser beams at the fiber core endface and the inner diaphragm surface, respectively, generating interference fringes. The reflected light travels back through the fiber and is detected by a photo-detector whereupon the reflection spectrum is recorded.

FIG. 18 shows the user interface of a Labview™ program running in the computer control that coordinates the tunable laser and the reflection spectra recording. "File storage directory" is used to set the file storage destination. "Full data display window" shows the whole data that has been obtained since the experiment started. "Partial data display window" shows the data that is chosen within a certain time which is determined by the "data display length adjust knob." "Sensor parameter input box" is used to prepare the sensor before the sensor is ready to be tested.

FIG. 19 shows one of the sensor's actual reflection spectra between 1520 nm and 1570 nm. The whole reflection spectrum fringe shifts from right to left when pressure applied to the sensor increases. The applied pressure is calculated based on the wavelength shift at the spectrum valley.

Prior to in vivo testing, each pressure sensor is calibrated in water, as described above, and packaged in a bio-compatible coil. First, the valley wavelength of the reflection spectrum is recorded with no additional pressure applied to the sensor. The valley wavelength is recorded again when a certain level of pressure, e.g., 10 mmHg, is applied on the sensor. The sensitivity of the sensor is given by $$\text{Sensitivity} = \frac{\text{Valley Wavelength(w.pressure)} - \text{Valley Wavelength(w.o.pressure)}}{10 \text{ mmHg} - 0}$$

The sensor shown in FIG. 17 was used in a pig study performed with approval of the Institutional Animal Care and Use Committee of the University of Massachusetts Medical School. Briefly, 25-50 kg Yorkshire swine were premedicated with intramuscular Glycopirrolate B (0.01 mg/kg) and an anesthetic cocktail (5 mg/kg Telazol; 2.5 mg/kg Ketamine; 2.5 mg/kg Xylazine) after which endotracheal intubation was performed. Anesthesia was maintained with inhalational 2-3% Isoflurane. Exposure of the left anterior descending coronary artery (LAD) was obtained via a median sternotomy, and 3.0 mm vascular occluder secured beyond the takeoff of the largest diagonal branch. Next, femoral arterial access was obtained via cutdown, and a 6 French arterial introducer sheath was inserted. Heparin was administered intravenously (50 units/kg), and a 6 French JR-4 guide catheter (Medtronic; Minneapolis, Minn.) advanced to the aortic arch. Baseline blood pressure measurements were obtained with standard invasive manometry. Optical spectral measurements were similarly obtained for comparison offline.

Next, the guiding catheter was introduced into the ostium of the left main coronary artery, and angiography was performed in the LAO projection. The optical sensor prototype wire was advanced into the LAD at a point beyond the vascular occluder. Pressure and spectral measurements were again obtained. The vascular occluder was deployed in order to create stenoses of various degrees as confirmed with repeat angiography. Spectral measurements were obtained beyond the stenosis to determine the correlation of stenosis severity with the anticipated shift in the optical spectrum.

Results indicate that the optical sensor accurately reflects invasive arterial hemodynamics. FIG. 20 shows the pressure tracing obtained from the aorta demonstrating the baseline blood pressure (67/39; MAP=50). The heart rate is 64 beats per minute, reflecting a cardiac cycle time of 0.94 second.

FIG. 21 demonstrates the pressure waveform detected by the optical fiber pressure sensor. Compared with FIG. 20, the waveform obtained by the optical fiber sensor is very similar. The optical fiber sensor shows the systolic pressure is 65 mmHg, the diastolic pressure is 38 mmHg, and heart rate is 64.4 bpm, consistent with the invasively transduced blood pressure.

The results also show that optical sensor identifies coronary stenosis-induced arterial pressure gradients. In order to determine whether the optical fiber pressure sensor is capable of detecting a decline in pressure generated by coronary stenoses, the optical spectral data were obtained in the presence or absence of critical stenoses of the LAD utilizing the surgically placed vascular occluder. FIG. 21 shows that mean coronary blood pressure obtained distal to the stenosis decreased from 50 mmHg to 45 mmHg in 20 seconds upon complete occlusion of the porcine LAD. Mean arterial pressure obtained at the coronary ostium with the standard transducer remained unchanged. Alleviation of the occlusion with partial deflation of the occluder resulted in an immediate response from the optical fiber sensor. FIG. 22 shows the blood pressure increase gradually from 43 mmHg to 47 mmHg. Deployment and deflation of the vascular occluder was repeated, whereupon the optically-detected pressure decreased from 49 mmHg to 45 mmHg and returned to 49 mmHg (FIG. 23).

The findings from this study demonstrate that the optical sensor prototype wire can discriminate pressure measurements obtained in vivo. The sensor accurately detected blood pressures transduced invasively. Importantly, the sensor was able to detect a decline in mean arterial blood pressure of the left anterior descending coronary artery when stenoses were created experimentally.

Currently, the waveform obtained by the optical fiber sensor is less detailed as compared with measurements obtained by catheter transduction. The most likely explanation is not due to the optical fiber sensor itself. Rather, the low sampling rate of the currently available tunable laser accounts for this finding. The sampling rate of current tunable laser is 8 points per cardio-cycle. An increase in the sampling rate of the tunable laser by 20 points per second would likely improve the detail of the optical fiber sensor and more closely correlate with catheter-transduced pressure waveforms.

While this invention has been particularly shown and described with references to example embodiments thereof, it will be understood by those skilled in the art that various changes in form and details may be made therein without departing from the scope of the invention encompassed by the appended claims.

What is claimed is:

1. A sensor comprising:
   a) an optical fiber; and
   b) a diaphragm of silica, which is formed by etching a silica-on-silicon wafer to remove the silicon, and having a surface in contact with the optical fiber and a thickness that varies by up to and including five percent, wherein a cavity is defined by a surface of the optical fiber and an inner surface of the diaphragm.

2. The sensor of claim 1, wherein an optical distance between the surface of the optical fiber and the inner surface of the diaphragm is about $(m+\frac{1}{2})(\lambda/4)$, where m is an integer equal to or greater than zero and $\lambda$ is a wavelength of light transmitted through the optical fiber.

3. The sensor of claim 1, wherein the optical fiber further includes a core aligned along a major axis of the optical fiber and a cladding disposed radially over at least a portion of the core.

4. The sensor of claim 3, wherein the surface of the optical fiber includes a surface of the core normal to the major axis of the optical fiber.

5. The sensor of claim 3, wherein the surface of the diaphragm in contact with the optical fiber is in contact with the cladding.

6. The sensor of claim 1, wherein the optical fiber and the diaphragm each include materials with nominal coefficients of thermal expansion.

7. The sensor of claim 1, wherein the diaphragm is formed using dry etching.

8. The sensor of claim 1, wherein the diaphragm is less than about three microns thick.

9. The sensor of claim 1, wherein the diaphragm is equal to or less than about one micron thick.

10. The sensor of claim 1, wherein at least a portion of the surface of the optical fiber is recessed within the optical fiber.

11. The sensor of claim 1, wherein at least a portion of the inner surface of the diaphragm is recessed within the diaphragm.

12. The sensor of claim 1, wherein the optical fiber is a multimode optical fiber and further including a single-mode fiber connected to the multimode optical fiber.

13. The sensor of claim 1, further including a coil surrounding the diaphragm and at least a portion of the optical fiber.

14. The sensor of claim 13, wherein the coil includes a tightly wound section disposed about the diaphragm.

15. The sensor of claim 14, wherein the coil includes a loosely wound section that extends distal to the tightly wound section.

16. The sensor of claim 1, wherein the inner surface of the diaphragm is smooth, with a root-mean-square roughness of about 0.2 nm over an area of about 20 µm×20 µm.

17. The sensor of claim 1, wherein the sensor is formed by a method comprising the steps of:
   (a) forming a thin film having a thickness that varies by up to and including five percent;
   (b) supporting the thin film on a holder; and
   (c) bonding the thin film to the optical fiber while the thin film is being supported on the holder, to thereby form the sensor with the diaphragm defining one side of the cavity.

18. The sensor of claim 17, wherein the thin film and the optical fiber are heated to at least 700 degrees Celsius to thermally bond the thin film to the optical fiber.

19. The sensor of claim 1, wherein the diameter of the diaphragm is the same as the diameter of the optical fiber.

20. The sensor of claim 1, wherein the silica diaphragm has a root-mean-square roughness of about 0.2 nm over an area of about 20 µm×20 µm.

* * * * *